(12) United States Patent
Koren

(10) Patent No.: US 10,512,629 B1
(45) Date of Patent: *Dec. 24, 2019

(54) COMPOSITIONS COMPRISING A CANNABINOID AND SPILANTHOL

(71) Applicant: SciCann Therapeutics Inc., Toronto (CA)

(72) Inventor: Zohar Koren, Gan Ner (IL)

(73) Assignee: SCICANN THERAPEUTICS INC., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/507,335

(22) Filed: Jul. 10, 2019

Related U.S. Application Data

(63) Continuation-in-part of application No. 16/241,682, filed on Jan. 7, 2019, which is a continuation of application No. PCT/IL2018/051000, filed on Sep. 6, 2018.

(60) Provisional application No. 62/555,752, filed on Sep. 8, 2017, provisional application No. 62/591,784, filed on Nov. 29, 2017.

(51) Int. Cl.
| | | |
|---|---|---|
| *A61K 36/00* | (2006.01) | |
| *A61K 31/352* | (2006.01) | |
| *A61P 1/16* | (2006.01) | |
| *A61K 31/16* | (2006.01) | |

(52) U.S. Cl.
CPC ............ *A61K 31/352* (2013.01); *A61K 31/16* (2013.01); *A61P 1/16* (2018.01)

(58) Field of Classification Search
CPC ..................................................... A61K 36/00
USPC ......................................................... 424/725
See application file for complete search history.

(56) References Cited

U.S. PATENT DOCUMENTS 3,720,762 A    3/1973  Hatasa et al.

FOREIGN PATENT DOCUMENTS

| WO | 2010010394 | 1/2010 |
| WO | 2017091764 | 6/2017 |

OTHER PUBLICATIONS

Arif et al., "A review on pharmacognostic and phytochemical study of a plant Spilanthes acmella Murr", The Pharma Innovation Journal, vol. 6, issue 5, pp. 172-177, May 31, 2017.
International Search Report and Written Opinion from International Application No. PCT/IL2018/051000 dated Oct. 24, 2018.

*Primary Examiner* — Michael V Meller
(74) *Attorney, Agent, or Firm* — The Roy Gross Law Firm, LLC; Roy Gross

(57) ABSTRACT

Provided herein are fixed-dose combination (FDC) compositions comprising therapeutically effective amounts of at least one cannabinoid and spilanthol whether as essentially pure isolates or synthetics or as components of essential oils or plant extracts or combinations thereof. The compositions are formulated as pharmaceutical compositions, nutraceuticals, cosmeceuticals, nutricosmetics, cosmetics, or food products. The pharmaceutical compositions are useful for the treatment of a gastro-enteric disease selected from the group consisting of irritable bowel disease, Crohn's disease, colitis, irritable bowel syndrome, and acute and chronic pancreatitis or of sepsis. Other pharmaceutical uses are as anti-allergic, anti-inflammatory, immunomodulator, antioxidant, anti-microbial, antibacterial, antifungal, antiviral, antinociceptive, analgesic, anesthetic, anti-cancer, apoptosis inducing, antiscorbutic, antipyretic, anti-malarial, addiction mitigatory, anxiolytic, anti-depressant, diuretic, anti-diarrheal, vasodilator or aphrodisiac agents. The pharmaceutical compositions of this invention exhibit a synergistic effect.

16 Claims, 7 Drawing Sheets

COMPOSITIONS COMPRISING A CANNABINOID AND SPILANTHOL

CROSS REFERENCE TO RELATED APPLICATIONS

This application is a Continuation-in-Part of U.S. patent application Ser. No. 16/241,682 filed on Jan. 7, 2019, which is National Phase of PCT Patent Application No PCT/IL2018/051000 having an International filing date of Sep. 6, 2018, which claims the benefit of priority to U.S. Provisional Patent Application No. 62/555,752 filed Sep. 8, 2017 and to U.S. Provisional Patent Application No. 62/591,784 filed Nov. 29, 2017, the entire contents of which are all hereby incorporated by reference in their entirety.

FIELD OF THE INVENTION

The present invention, in some embodiments thereof, relates to fixed dose combination (FDC) compositions, more particularly, but not exclusively, to compositions comprising at least one cannabinoid as a plant isolate or synthetic, in essentially pure form or as a component of a plant extract or essential oil and spilanthol as an isolate or synthetic, in essentially pure form or as a component of a plant extract or essential oil, or combinations thereof. The combination compositions of this invention are useful for the treatment, prevention or amelioration of medical conditions and exhibit strong synergistic effects.

BACKGROUND

An FDC drug, also known as combination drug, is a fixed-dose combination, which includes two or more active pharmaceutical ingredients (APIs), combined in a single dosage form, which is manufactured and distributed in fixed doses.

The vast medicinal potential of plants has been appreciated by humans long before recorded history.

Traditional medicine utilizing medicinal plants and plant extracts has been practiced for centuries in parallel to modern Western medicine. Among the more than 300,000 seed plants, some 60% have been utilized for therapeutic interventions, particularly in South America, Africa, and Asia.

Cannabis, more commonly known as marijuana, is a genus of flowering plants that includes at least three species, *Cannabis sativa*, *Cannabis indica*, and *Cannabis ruderalis* as determined by plant phenotypes and secondary metabolite profiles.

Several medicinal uses have been found for the active ingredients of *cannabis*, mainly the cannabinoids cannabidiol (CBD), tetrahydrocannabinol (THC), cannabinol (CBN), and cannabichromene (CBC). For example, treatment of nausea and pain associated with cancer and chemotherapy, nausea, pain associated with AIDS, arthritis and rheumatism, migraines, stress and depression, to mention a few.

Spilanthol, also known as affinin (C14H23NO, MW: 221.339 g/mol) is a secondary metabolite bioactive N-alkylamide compound found in many different plants having several biological properties and health effects. Spilanthol is present, for example, in the genus *Heliopsis longipes* also known as chilcuague and in several species in the genus *Acmella*, for example, *A. oleracea*, also known as paracress and jambu.

Like many plant-originated alkamides, spilanthol (affinin) presents various bioactivities, from helping to protect the plant to being an antioxidant, antimutagenic, anti-cancer, antinociceptive, anti-inflammatory, antimicrobial, antibacterial, antifungal, analgesic and endocannabinoid agonist.

SUMMARY OF THE INVENTION

The present invention provides fixed dose combination compositions (FDCs), more specifically, compositions comprising at least one cannabinoid as a plant isolate or synthetic in essentially pure form or as a component of a plant extract or essential oil and spilanthol as an isolate or synthetic, in essentially pure form or as a component of a plant extract or essential oil or combinations thereof. Also provided are methods of treatment of a number of medical conditions by administration to a patient in need thereof therapeutically effective amounts of the above compositions.

In some embodiments there is provided a composition comprising at least one cannabinoid as an isolate or synthetic, in essentially pure form or as a component of a plant extract or essential oil and spilanthol as an isolate or synthetic.

In some other embodiments of the invention there is provided a composition comprising a cannabinoid-containing plant extract or essential oil and spilanthol.

In some embodiments, the composition comprises *cannabis* plant material selected from *cannabis* extract, *cannabis* essential oil or both, and further comprises spilanthol-containing plant material selected from spilanthol-containing extract, spilanthol-containing essential oil or both.

In some embodiments, the composition comprises *cannabis* plant essential oil and spilanthol-containing essential oil.

In some embodiments, the composition provided herein comprises *cannabis* plant material selected from *cannabis* extract or *cannabis* essential oil and spilanthol.

In some embodiments, the composition provided herein comprises at least one cannabinoids and spilanthol-containing plant material selected from spilanthol-containing extract or spilanthol-containing essential oil or both.

In some embodiments, the composition provided herein comprises at least one cannabinoid and spilanthol.

In some embodiments, the *cannabis* plant material provided to the composition is obtained from a *cannabis* plant selected from the group consisting of *Cannabis sativa*, *Cannabis indica*, and *Cannabis ruderalis*.

In some embodiments, the spilanthol-containing plant material is obtained from at least one species of the genus Heliopsis, *Acmella*, or *Wedelia*. In some embodiments, the at least one species are selected from *A. ciliata*, *A. oppositifolia*, *A. radicans*, *A. brachyglossa*, *A. oleracea*, *A. paniculata*, *A. uliginosa*, *Heliopsis longipes* (chilcuague), *H. scabra* Dunal, *H. parvifolia* A. Gray and *H. gracilis* Nutt., *H. aff. novogaliciana* B. L. Turner, *H. procumbens* Hemls, *H. annua* Hemls and *W. parviceps* Blake.

In some embodiments, the species is Heliopsis *longipes* (chilcuague).

In some embodiments, spilanthol is the olefinic isobutylamide having the molecular formula C14H23NO, isomers, derivatives, salts and metabolites thereof.

In some embodiments, the composition provided herein comprises at least one cannabinoid selected from the group consisting of tetrahydrocannabinol (THC), iso-tetrahydrocannabinol (iso-THC), tetrahydrocannabinolic acid (THCA), cannabidiol (CBD), cannabidiolic acid (CBDA), cannabinol (CBN), cannabinolic acid (CBNA), cannabinol methyl ether (CBNM), cannabinol-C4 (CBN-C4), cannabinol-CZ (CBN-C2), cannabiorcol (CBN-C1), cannabinodiol (CBND), cannabigerol (CBG), cannabigerolic acid (CBGA), cannabigerolic acid monomethyl ether (CBGAM), cannabigerol monomethyl ether (CBGM), cannabigerovarinic acid (CBGVA), cannabichromene (CBC), cannabichromanon (CBCN), cannabichromenic acid (CBCA), cannabichromevarin (CBCV), cannabichromevarinic acid (CBCVA), tetrahydrocannabivarin (THCV), cannabidivarin (CBDV), cannabielsoin (CBE), cannabielsoic acid A (CBEA-A), cannabielsoic acid B (CBEA-B), cannabigerovarin (CBGV), cannabidiolic acid (CBDA), cannabidiol monomethyl ether (CBDM), cannabidiol-C4 (CBD-C4), cannabidivarinic acid (CBDVA), and cannabidiorcol (CBD-C1), cannabicyclol (CBL), cannabicyclolic acid (CBLA), cannabicyclovarin (CBLV), cannabitriol, cannabitriolvarin (CBTV), ethoxy-cannabitriolvarin (CBTVE), cannabivarin (CBV), cannabidivarin (CBVD), cannabitriol, cannabitriolvarin (CBTV), ethoxy-cannabitiolvarin (CBTVE), cannabifuran (CBF), dehydrocannabifuran (DCBF), and cannabiripsol (CBR), pharmaceutically acceptable salts thereof, solvates, metabolites, metabolic precursors, isomers or derivatives thereof.

In some embodiments, the at least one cannabinoid is THC and/or CBD.

In some embodiments, the composition provided herein is formulated in the form a pharmaceutical composition, a nutraceutical, a cosmeceutical, a nutricosmetic, a cosmetic composition, a body care product, a personal hygiene product or a food product.

In some embodiments, the composition provided herein is formulated as a single unit dosage form comprising spilanthol-containing plant material and/or spilanthol and, cannabis plant material and/or at least one cannabinoid. In some embodiments, the composition is formulated as two or more units of dosage form, at least one of which comprises spilanthol, spilanthol-containing extract or spilanthol-containing essential oil, and at least one dosage form comprises cannabis plant extract, cannabis plant essential oil, or at least one cannabinoid. In some embodiments, the composition provided herein is a pharmaceutical composition selected from an anti-allergic agent, an anti-inflammatory agent, an immunomodulator, an antioxidant, an anti-microbial agent, an antibacterial agent, an antifungal agent, an antiviral agent, an antinociceptive agent, an analgesic agent, an anesthetic agent, an anti-cancer agent, an apoptosis inducing agent, an antiscorbutic agent, an antipyretic agent, an anti-malarial agent, an addiction mitigatory agent, an anxiolytic agent, an anti-depressant agent, a diuretic agent, an anti-diarrheal agent, a vasodilator and an aphrodisiac agent.

The pharmaceutical composition provided herein is useful in alleviating, treating, curing, mitigating or preventing a disease or condition selected from cancer, headaches, fever, cough, cold, inflammation, autoimmune diseases, allergy, bacterial, fungal or viral infections, vertigo, body aches, indigestive problems, obesity, anxiety, sepsis, depression, glaucoma and snake bite. In some embodiments, the pharmaceutical composition provided herein is useful in alleviating, treating, curing, mitigating or preventing inflammatory disease.

In some embodiments, the composition provided herein is a cosmeceutical or nutricosmetic In some embodiments, the composition provided herein is a cosmetic composition selected from an anti-wrinkle composition, a moisturizing cream, a face mask a makeup, and a lipstick.

In some embodiments, spilanthol and the at least one cannabinoid, cannabis plant extract, or a cannabis plant essential oil are administered together.

In some embodiments, spilanthol and the at least one cannabinoid, cannabis plant extract, or a cannabis plant essential oil are administered consecutively.

In some embodiments, the method provided herein comprises administration of a composition as provided herein.

In some embodiments, the disease, disorder or medical condition that is treatable, curable, mitigated or alleviated is selected from a gastro-enterologic disease, inflammation, an autoimmune disease, an immunodeficiency disease, a neurodegenerative disease, an oncologic disease, a cardiovascular disease, a mental or psychiatric disease, a skin disease, viral, bacterial or fungal infection, and blood vessels diseases or disorders.

In some embodiments, the disease, disorder or medical condition that is treatable, curable, mitigated or alleviated by any of the compositions provided herein is selected from nausea, appetite lose and pain associated with cancer and chemotherapy; nausea, appetite lose, pain and wasting associated with AIDS; toothache; cancer; arthritis and rheumatism; glaucoma; migraine; scurvy; muscle spasticity; alcohol and narcotics withdrawal; stress; asthma; Tourette syndrome, Cervical dystonia; epileptic seizures; dementia; dysmenorrhea; anxiety disorders; depression; diabetes; diarrhea; neuropathic pain; chronic pain; psoriasis; dermatitis; swimmer's eczema; Alzheimer's disease; Huntington disease; Parkinson; Lyme disease; post-traumatic stress disorder; malaria; vasoconstriction, allergy; edema; liver inflammation; schizophrenia; colitis; painful spasms; fibromyalgia; sexual disfunction; posttraumatic stress disorder (PTSD); sepsis; necrotizing soft tissue infections (NSTI); acute and chronic pancreatitis; opioid addiction; inflammatory bowel disease (IBD); non-alcoholic fatty liver disease (NAFLD); and irritable bowel syndrome (IBS). In some embodiments, co-administration of spilanthol and at least one cannabinoid results in a therapeutic effect selected from a synergistic effect, an additive effect, a potentiating effect and any combination thereof.

According to another aspect, there is provided a method of treating, ameliorating or preventing non-alcoholic steatohepatitis (NASH) in a subject in need thereof, comprising co-administering to said subject a therapeutically effective amount of cannabidiol (CBD) and a therapeutically effective amount of spilanthol.

According to some embodiments, the administering a therapeutically effective amount of CBD comprises administering a pharmaceutical composition comprising CBD.

According to some embodiments, the administering a therapeutically effective amount of spilanthol comprises administering a pharmaceutical composition comprising spilanthol.

According to some embodiments, the co-administering a therapeutically effective amount of CBD and a therapeutically effective amount of spilanthol comprises administering a pharmaceutical composition comprising CBD and spilanthol. According to some embodiments, the pharmaceutical composition comprising CBD and spilanthol is a fixed-dose composition comprising both CBD and spilanthol.

According to some embodiments, the CBD and spilanthol are administered separately According to some embodiments, the CBD is essentially pure, comprising a purity of at least 95%. According to some embodiments, the CBD is a component of a *cannabis* essential oil or extract.

According to some embodiments, the spilanthol is essentially pure, comprising a purity of at least 95%. According to some embodiments, the spilanthol is a component of a spilanthol-containing essential oil or extract.

According to some embodiments, the therapeutically effective amount of CBD is from 5 mg to 500 mg.

According to some embodiments, the therapeutically effective amount of spilanthol is from 1 mg to 100 mg.

According to some embodiments, the NASH is fibrotic or non-fibrotic NASH. According to some embodiments, the NASH is cirrhotic or non-cirrhotic NASH.

According to some embodiments, the CBD is administered before, after or concomitantly with said spilanthol.

According to some embodiments, the treating, ameliorating or preventing comprises reducing at least one symptom of NASH, wherein said symptom is selected from:
a. increased activity of at least one liver enzyme;
b. increased levels of at least one pro-inflammatory cytokine; and
c. liver weight loss.

According to some embodiments, the at least one liver enzyme is selected from alanine aminotransferase and aspartate aminotransferase.

According to some embodiments, the pro-inflammatory cytokine is IL-6.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DETAILED DESCRIPTION OF THE INVENTION

Figure 1:
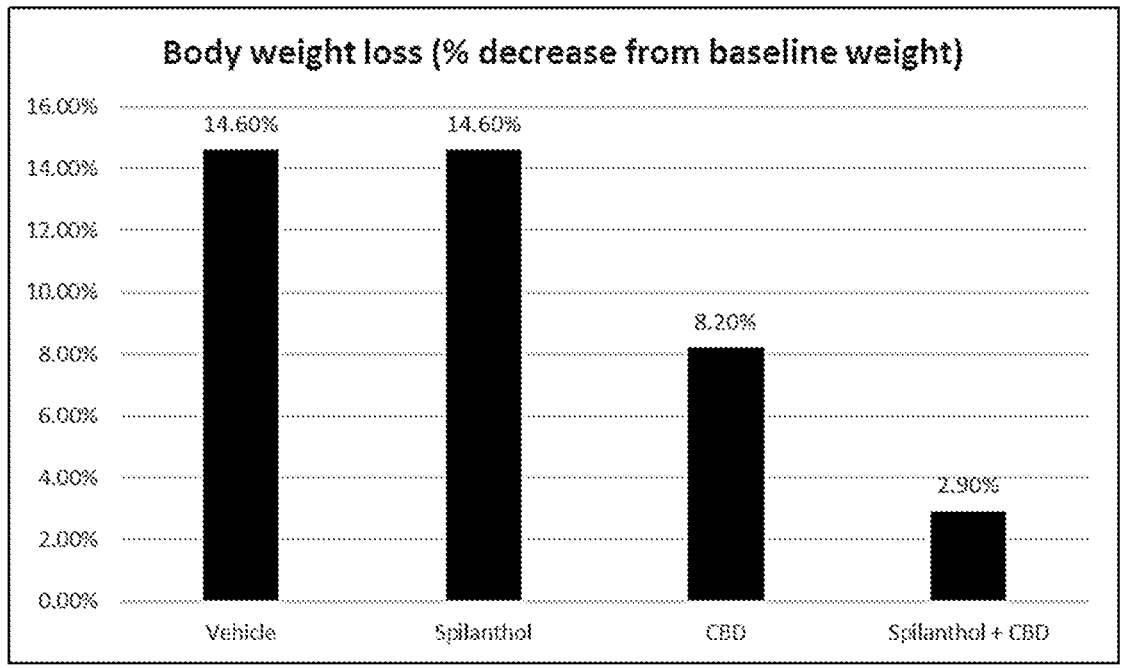
FIG. 1 depicts the body weight loss (% decrease from baseline weight of the mice after treatment with vehicle, spilanthol, CBD or spilanthol+CBD.

The present invention provides fixed-dose combination (FDC) compositions comprising therapeutically effective amounts of at least one cannabinoid and spilanthol.

In some embodiments, the FDC compositions comprise at least one cannabinoid and spilanthol (spilanthol), whether as isolates from a plant source or synthetic, being essentially pure and having an assay of at least 95%, preferably at least 98%.

In some other embodiments, the at least one cannabinoid in the FDC composition is cannabidiol (CBD).

The at least one cannabinoid and spilanthol may be sourced as plant extracts or essential oils, but also as essentially pure isolates from plants or essentially pure synthetic raw materials.

The isolates and synthetic cannabinoids and spilanthol have some advantages over the respective plant extracts or essential oils.
1. The isolates and synthetic cannabinoids and spilanthol are essentially free of impurities, the nature and percentage of which are somewhat unpredictable as they depend on the plant source, seasonal factors, extraction process, etc.
2. The drug dosages are very easy to manufacture, because you just weigh and compound the actives.
3. Some of the *cannabis* plant extract components may have a hallucinogenic affect, which is undesirable in a drug.
4. Solid isolate actives are easier to formulate than oils.

An isolate is an active agent (in our case a cannabinoid or spilanthol, isolated from a botanical source (a plant) and subsequently purified.

Just as an example, CBD (one of the important cannabinoids of this invention, is available as a CBD isolate.

CBD isolate is all-natural cannabidiol in its purest form. CBD isolate is typically offered in a fine white powder containing 99% pure cannabidiol.

The isolate gives patients complete control of exactly how much CBD goes into each serving. Because CBD isolate is over 99% pure, each milligram of CBD isolate represents a milligram of active CBD.

Some cannabinoids may be obtained by chemical synthesis. The synthesis of CBD has been accomplished by several research groups: "Synthese and Chiralität des (−)-Cannabidiols". Helv. Chim. Acta. 50 (2): 719-723, Gaoni Y, Mechoulam R (1985). "Boron trifluoride etherate on alumina—a modified Lewis acid reagent. An improved synthesis of cannabidiol". Tetrahedron Letters. 26 (8): 1083-1086.

In some embodiments, the spilanthol used in the composition described herein is the isomer (2E,6Z,8E)-N-isobutyl-2,6,8-decatrienamide presented by the formula (1):

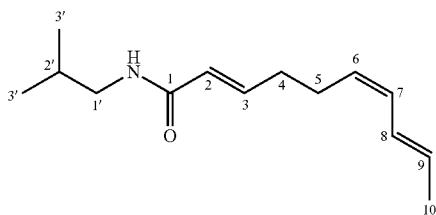

and this isomer may be chemically synthesized or isolated and purified from any of the spilanthol-producing plants described above.

Chemically synthesized spilanthol is usually, but not exclusively, synthesized starting from the appropriate unsaturated acid by amidation with a simple aliphatic amine. Spilanthol may be synthesized using any of the routes known in the art, and described for example, in: Ikeda et al., Tetrahedron Lett., 25: pp. 5177-5180, (1984); Jacobson, Chem. Ind., 2: pp. 50-551957; Ley et al., Dev. Food Sci., 43: pp. 21-24, (2006); Rios and Olivo, Atta-Ur-Rahman (Ed.), Studies in Natural Products Chemistry, Elsevier, New York, pp. 79-118, (2014), all of which are herein incorporated by reference.

The stereoselective synthesis of isomer of formula (1) usually provides a 61% yield of the light-yellow powder with a melting point of 23° C., a boiling point of 165° C., a refractive index at 298.0 of 1.5135 and a maximum UV absorption at 228.5 nm. Its IR spectrum has the following major peaks: max (film) cm−1: 3340, 3150, 3080, 3020, 1678, 1636, 1550, 1240, 1160, 987, 953. It has a monoisotopic molecular weight of 221.177963 Da.

Relatively pure spilanthol isolates as well as extracts from a number of plants are commercially available from a number of sources. Pharmaceutical use may require further purification.

In some embodiments, there is provided a fixed-dose combination (FDC) composition comprising therapeutically effective amounts of at least one cannabinoid and spilanthol and a pharmaceutically acceptable carrier.

According to some embodiments, in the above FDC combination composition, the at least one cannabinoid and the spilanthol, whether isolate or synthetic, are essentially pure having an assay of at least 95%, preferably at least 98%.

In some embodiments, in the above FDC combination composition, the at least one cannabinoid is a component of a *cannabis* essential oil or extract and spilanthol is a component of a spilanthol-containing essential oil or extract.

In some other embodiments, in the above FDC combination composition, the at least one cannabinoid, whether isolate or synthetic is essentially pure having an assay of at least 95%, preferably at least 98% and spilanthol is a component of a spilanthol-containing essential oil or extract.

According to some embodiments, in the above FDC combination composition, the at least one cannabinoid is a component of a *cannabis* essential oil or extract and spilanthol is an essentially pure spilanthol isolate or essentially pure synthetic spilanthol.

In some embodiments, the above FDC combination composition further comprises at least one additional ingredient selected from phytochemicals, an essential oil, a carrier oil, an antibacterial agent, an antioxidant (e.g., ascorbic acid or sodium bisulfite), an anti-inflammatory agent, anti-viral agent, an antifungal agent, an anti-microbial agent, a chemotherapeutic agent, an immune-oncology (IO) agent, an immune-apoptosis inducing agent, an anti-diarrheal agent, an anti-histamine, a probiotic, a vitamin, a colorant, a buffer, an emulsifier, a sun screen, a moisturizer, an analgesic agent, an anti-depressant agent, a skin nutrient, a medicinal herbal extract, a flavor, a flower essence, a protein, a lubricant, a buffering agent, a bulking agent (e.g. mannitol), a physiologically suitable carrier, and an inactive excipient.

According to some embodiments, said *cannabis* essential oil or extract is obtained from a plant selected from the group consisting of *Cannabis sativa, Cannabis indica, Cannabis ruderalis* and mixtures thereof.

According to some other embodiments, said spilanthol-containing extract or the spilanthol-containing essential oil in the above FDC combination composition is obtained from at least one species of the genus *Heliopsis, Acmella,* or *Wedelia*, wherein the species are selected from *A. ciliata, A. oppositifolia, A. radicans, A. brachyglossa, A. oleracea, A. paniculata, A. uliginosa, Heliopsis longipes* (chilcuague), *H. scabra* Dunal, *H. parvifolia* A. Gray and *H. gracilis* Nutt., *H. aff. novogaliciana* B. L. Turner, *H. procumbens* Hemls, *H. annua* Hemls and *W. parviceps* Blake.

According to some embodiments, the at least one cannabinoid in the above FDC combination composition is selected from the group consisting of tetrahydrocannabinol (THC), iso-tetrahydrocannabinol (iso-THC), tetrahydrocannabinolic acid (THCA), cannabidiol (CBD), cannabidiolic acid (CBDA), cannabinol (CBN), cannabinolic acid (CBNA), cannabinol methyl ether (CBNM), cannabinol-C4 (CBN-C4), cannabinol-CZ (CBN-C2), cannabiorcol (CBN-C1), cannabinodiol (CBND), cannabigerol (CBG), cannabigerolic acid (CBGA), cannabigerolic acid monomethyl ether (CBGAM), cannabigerol monomethyl ether (CBGM), cannabigerovarinic acid (CBGVA), cannabichromene (CBC), cannabichromanon (CBCN), cannabichromenic acid (CBCA), cannabichromevarin (CBCV), cannabichromevarinic acid (CBCVA), tetrahydrocannabivarin (THCV), cannabidivarin (CBDV), cannabielsoin (CBE), cannabielsoic acid A (CBEA-A), cannabielsoic acid B (CBEA-B), cannabigerovarin (CBGV), cannabidiolic acid (CBDA), cannabidiol monomethyl ether (CBDM), cannabidiol-C4 (CBD-C4), cannabidivarinic acid (CBDVA), and cannabidiorcol (CBD-C1), cannabicyclol (CBL), cannabicyclolic acid (CBLA), cannabicyclovarin (CBLV), cannabitriol, cannabitriolvarin (CBTV), ethoxy-cannabitiolvarin (CBTVE), cannabivarin (CBV), cannabidivarin (CBVD), cannabitriol, cannabitriolvarin (CBTV), ethoxy-cannabitiolvarin (CBTVE), cannabifuran (CBF), dehydrocannabifuran (DCBF), and cannabiripsol (CBR), combinations thereof, pharmaceutically acceptable salts thereof, solvates, metabolites, metabolic precursors, isomers or derivatives thereof.

In some embodiments, the at least one cannabinoid in the above FDC combination composition is CBD.

In some embodiments, the at least one cannabinoid in the above FDC combination composition is THC.

According to some embodiments, the above FDC combination composition is formulated in the form of a pharmaceutical composition, a nutraceutical, a cosmeceutical, a nutricosmetic, a cosmetic composition, a body care product, a personal hygiene product or a food product.

According to some other embodiments, the above FDC combination composition is formulated as a single unit dosage form comprising therapeutically effective amounts of spilanthol and at least one cannabinoid.

According to some other embodiments, the above FDC combination composition is formulated as two or more units of dosage forms, at least one of which comprises essentially pure spilanthol, a spilanthol-containing extract or a spilanthol-containing essential oil, and at least one dosage form comprises *cannabis* plant extract, *cannabis* plant essential oil, or at least one essentially pure cannabinoid.

In some embodiments, the above FDC combination composition is a pharmaceutical composition selected for use as anti-allergic, anti-inflammatory, immunomodulator, antioxidant, anti-microbial, antibacterial, antiacne, antifungal, antiviral, antinociceptive, analgesic, anesthetic, anti-cancer, apoptosis inducing, anti scorbutic, antipyretic, anti-malarial, addiction mitigatory, anxiolytic, anti-depressant, diuretic, anti-diarrheal, vasodilator or aphrodisiac.

In some embodiments, there is provided a method of treatment, prevention or amelioration of a condition amenable to treatment, prevention or amelioration by administration to a patient in need thereof of the above combination composition, comprising therapeutically effective amounts of at least one cannabinoid and spilanthol.

In some other embodiments, the above condition amenable to treatment is a gastro-enteric disease.

According to some embodiments, there is provided the above method of treatment, wherein the at least one cannabinoid is CBD and the condition is a gastro-enteric disease and wherein the method comprises the administration to a patient in need thereof a composition comprising 150 mg CBD and 30 mg spilanthol (5:1 ratio), 250 mg CBD and 50 mg spilanthol (5:1 ratio), 100 mg CBD and 10 mg spilanthol (10:1 ratio) or 500 mg CBD or 25 mg spilanthol (20:1 ratio).

According to some other embodiments there is provided the above method of treatment, wherein the gastro-enteric disease is selected from the group consisting of irritable bowel disease (IBD), Crohn's disease, colitis, irritable bowel syndrome, and acute or chronic pancreatitis.

According to some other embodiments there is provided the above method of treatment, wherein the condition is sepsis.

According to some other embodiments there is provided the above method of treatment, wherein the condition is an autoimmune disease.

In some embodiments, the autoimmune disease is: Addison's disease, Agammaglobulinemia, Alopecia areata, Amyloidosis, Ankylosing spondylitis, Anti-GBM/Anti-TBM nephritis, Antiphospholipid syndrome, Autoimmune hepatitis, Autoimmune inner ear disease, Axonal and neuronal neuropathy, Behcet's disease, Bullous pemphigoid, Castleman disease, Celiac disease, Chagas disease, Chronic inflammatory demyelinating polyneuropathy, Chronic recurrent multifocal osteomyelitis, Cicatricial pemphigoid/benign mucosal pemphigoid, Churg-Strauss, Cogan's syndrome, Cold agglutinin disease, Congenital heart block, Coxsackie myocarditis, CREST syndrome, Crohn's disease, Dermatitis herpetiformis, Dermatomyositis, Devic's disease, Discoid lupus, Dressier's disease, Endometriosis, Eosinophilic esophagitis, Eosinophilic fasciitis, Erythema nodosum, Essential mixed cryoglobulinemia, Evans syndrome, Fibromyalgia, Fibrosing alveolitis, Giant cell arteritis, Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura, Herpes gestationis or pemphigoid gestationis, Hypogammalglobulinemia, IgA Nephropathy, IgG4-related sclerosing disease, Inclusion body myositis, Interstitial cystitis, Juvenile arthritis, Juvenile diabetes, Juvenile myositis, Kawasaki disease, Lambert-Eaton syndrome, Leukocytoclastic vasculitis, Lichen planus, Lichen sclerosus, Ligneous conjunctivitis, Linear IgA disease, Lupus, chronic Lyme disease, Meniere's disease, Microscopic polyangiitis, Mixed connective tissue disease, Mooren's ulcer, Mucha-Habermann disease, Multiple sclerosis, Myasthenia gravis, Myositis, Narcolepsy, Neuromyelitis optica, Neutropenia, Ocular cicatricial pemphigoid, Optic neuritis, Palindromic rheumatism, PANDAS, Paraneoplastic cerebellar degeneration, Paroxysmal nocturnal hemoglobinuria, Parry Romberg syndrome, Pars planitis, Parsonnage-Turner syndrome, Pemphigus, Peripheral neuropathy, Perivenous encephalomyelitis, Pernicious anemia, POEMS syndrome, Polyarteritis *nodosa*, Polymyalgia rheumatic, Postmyocardial infarction syndrome, Postpericardiotomy syndrome, Polymyositis, Primary biliary cirrhosis, Primary sclerosing cholangitis, Progesterone dermatitis, Psoriasis, Psoriatic arthritis, Pure red cell aplasia, Pyoderma gangrenosum, Raynaud's phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm and testicular autoimmunity, Stiff person syndrome, Subacute bacterial endocarditis, Susac's syndrome, Sympathetic ophthalmia, Takayasu's arteritis, Temporal arteritis/Giant cell arteritis, Thrombocytopenic purpura, Tolosa-Hunt syndrome, Transverse myelitis, Type 1 diabetes, Ulcerative colitis, Undifferentiated connective tissue disease, Uveitis, Vasculitis, Vitiligo, and/or Wegener's granulomatosis. In one embodiment, the autoimmune disease is autoimmune hepatitis.

In some other embodiments, there is provided the above method of treatment, wherein co-administration of a composition comprising spilanthol and at least one cannabinoid results in a therapeutic effect selected from a synergistic effect, an additive effect, a potentiating effect and any combination thereof.

According to some embodiments, there is provided the above method of treatment, wherein the co-administration of a composition comprising at least one cannabinoid and spilanthol exhibits a synergistic therapeutic effect of at least 100%, at least 300% or at least 500% higher than the therapeutic effect of the at least one cannabinoid or of spilanthol respectively, administered separately in a similar amount.

According to some embodiments, there is provided the above method of treatment, wherein the at least one cannabinoid is CBD.

According to some other embodiments, there is provided the above method of treatment wherein the at least one cannabinoid is THC.

According to some embodiments, the composition of this invention is formulated as a body lotion, soap, body wash, moisturizer, self-tanner, hand cream, body scrub, sunscreen, bath product, toothpaste, soap, shampoo, mouth wash, deodorant, antiperspirant, or shaving soap.

According to some embodiments, the composition of this invention is a cosmetic composition selected from an anti-wrinkle composition, a moisturizing cream, a face mask, a makeup, and a lipstick.

According to some other embodiments, the composition of this invention is a body care product or a personal hygiene product, selected from a body lotion, a soap, a body wash, a moisturizer, a self-tanner, a hand cream, a body scrub, a sunscreen, a bath product, a toothpaste, a shampoo, a mouth wash, a dental floss, a deodorant, an antiperspirant, and a shaving product.

The term "pure" or "essentially pure" as used herein for "pure spilanthol" and "pure cannabinoid" is meant to describe the compound per se, a clean, stand-alone chemical entity which is not in the form of, or a component of an extract or essential oil.

The term "extract" as used herein refers to a crude plant extract which is a collection of crude mixtures extracted from different parts of a plants, for example, flowers, roots, stem, leaves. The general procedures adopted for obtaining plant extract are collection of plant parts, drying, for example, air drying, powdering and extraction with water or solvents (polar, non-polar or both). The crude extract is produced by evaporating the solvent. The extract is further purified or concentrated to obtain a "fine extract" used for isolation or separation of classes of compounds from the extract (alkaloids, tannins, phenolics, terpenoids etc.), or pure compounds by further processing the extract.

As used herein, the terms spilanthol and affinin are used interchangeably.

As used herein, the terms" plant essential oil", "essential oil" and "oil" are interchangeable and refer to natural plant oil typically obtained by distillation, and having a chemical composition and organoleptic properties (e.g., fragrance) characteristic of the plant or other source from which it is extracted. The process of acquiring a plant's essential oil is a little more complex than extraction, as it must be obtained through distillation (hydro, steam or hydro-cum-steam). The liquid that is distilled off is the plant essence, and the very small amount of volatile liquid that is left behind is the essential oil. By further processing or distilling, essential oils may sometimes be obtained from extracts. To be noted, "essential oil" and "oil" as used herein constitutes the natural, volatile plant oil obtained by distillation of plant biomass, and essential oil obtained by refining a plant extract as defined herein, by subjecting it to further processes such as distillation.

Embodied compositions described herein comprise either plant extracts or plant essential oils, or both.

The terms "*cannabis* oil" (or the interchangeable terms "*cannabis* plant oil" and "*cannabis* plant essential oil") and "*cannabis* extract" (or the interchangeable term "*cannabis* plant extract") as used herein, refer to a mixture of compounds obtained from the distillation and extraction of *cannabis* plants, respectively.

*Cannabis* essential oil is a concentrated, sticky, green liquid and is considered highly volatile.

"Cannabinoid" as used herein is a chemical compound that shows direct or indirect activity at a cannabinoid receptor (CNR). There are two main cannabinoid receptors, CNR1 (also known as CB1) and CNR2 (also known as CB2). Other receptors that have been indicated as having cannabinoid activity include the GPR55, GPR18, and TRPV1 receptors.

Cannabinoids, as referred to herein, include chemically synthesized cannabinoids and "phytocannabinoids", namely cannabinoids that occur in a plant species or are derived from cannabinoids produced, e.g., by a *cannabis* plant species. Cannabinoids as used herein further include pharmaceutically acceptable salts, solvates, metabolites, metabolic precursors, isomers or derivatives of cannabinoids.

To be noted, although spilanthol may show direct or indirect activity at a CNR, it is excluded herein from the scope of cannabinoids and phytocannabinoids.

As used herein, the term "at least one cannabinoid" is meant to refer to one cannabinoid or a combination of at least two cannabinoids, for example, any combination of two, three, four, five, six, ten or even more of any of the cannabinoids defined or described herein, whether naturally occurring cannabinoids (phytocannabinoids), chemically synthetized cannabinoid, or pharmaceutically acceptable salts thereof, solvates, metabolites, metabolic precursors, isomers or derivatives thereof.

In some embodiments, the composition described herein comprises THC and/or CBD.

As used herein the term "cannabidiol" or "CBD" refers to the major non-psychotropic cannabinoid in most *cannabis* preparations, such as hashish and marihuana. Thus, cannabidiol, as used herein, is meant to refer to 2-[3-methyl-6-(1-methylethenyl)-2-cyclohexen-1-yl]-5-pentyl-1,3-benzenediol, whether the naturally occurring sub stance or synthetic versions of same, as well as to pharmaceutically acceptable salts, solvates, metabolites (e.g., cutaneous metabolites), and metabolic precursors of CBD. Some cannabidiol derivatives and metabolites thereof are taught, for example, in U.S. Pat. Nos. 7,759,526, 8,119,697 and 8,435,556, each of which is hereby incorporated by reference in its entirety. The synthesis of CBD is described, for example, in Petilka et al., Helv. Chim. Acta, 52:1102 (1969) and in Mechoulam et al., J. Am. Chem. Soc., 87:3273 (1965), which are hereby incorporated by reference.

As used herein the term "tetrahydrocannabinol" or "THC", or more precisely its main isomer (−)-trans-Δ9-tetrahydrocannabinol ((6aR,10aR)-delta-9-tetrahydrocannabinol), is the principal psychoactive cannabinoid of some strains of *cannabis*. The term refers to the naturally occurring substance or synthetic versions of same. Herein, THC, also refers to pharmaceutically acceptable salts, solvates, metabolites, and metabolic precursors of (−)-trans-Δ9-tetrahydrocannabinol. Δ9-tetrahydrocannabinol is marketed under the generic name "dronabinol".

The cannabinoids, for example, THC and/or CBD can be provided to the composition described herein in a purified form (e.g., above 90% purity, e.g., synthetic forms) or in a *cannabis* essential oil (e.g., obtained from trichome extract). The oil can be extracted from a single strain of a *cannabis* or from a plurality of strains (or genetic backgrounds), wherein the *cannabis* genetic background is selected according to the intended use, for example, high/low CBD/THC levels.

The olefinic isobutylamide (C14H23NO, 221.339 g/mol), named spilanthol or affinin is a bioactive alkamide found in many different plants, e.g., of the family Asteraceae (also known as Compositae), tribe Heliantheae, and subtribe Ecliptinae, that are used as traditional remedies throughout the world since ancient times, mainly for the alleviation of toothache, pneumonia and bronchitis (Molina-Torres et al., Biochem. Syst. Ecol. 24: 27-43, 1996; Prachayasittukal et al., EXCLI J. 12: 291-312, 2013; Paulraj et al., Adv. Pharmacol. Sci., http://dx.doi.org/10.1155/2013/510298, 2013; Rios and Olivo, Natural and synthetic alkylamides: applications in pain therapy. In: *Atta*-Ur-Rahman (Ed.), Studies in Natural Products Chemistry. Elsevier, New York, pp. 79-118, 2014).

Spilanthol may be extracted and purified, for example, from the genera *Acmella*, Heliopsis and Wedelia of the family Asteraceae.

Non-limiting examples of spilanthol extraction processes include use of ethanol:water (7:3, v/v) to solubilize spilanthol from dried flowers, use of ultrasonication and ethanol:hexane (3:7, v/v) at 50° C. to solubilize spilanthol from dried flowers, use of supercritical CO2 with added ethanol and water to extract spilanthol from *S. acmella* flowers, leaves and stems.

After being extracted, spilanthol can be separated from the other components in the extract, and subsequently purified using any of the methods and techniques known in art, for example, by molecular distillation, thin-film distillation, or a chromatography method such as preparative scale thin layer chromatography (TLC) and/or high-pressure liquid chromatography (HPLC), and such purification methods may be used alone or in appropriate combinations to obtain high yield of pure spilanthol.

In some embodiments, the composition described herein comprise spilanthol-containing extract and/or spilanthol-containing essential oil.

The terms "spilanthol-containing extract" and "spilanthol-containing essential oil" (or, interchangeably, "affinin-containing oil") as used herein, refer to a mixture of compounds obtained from the extraction/distillation of spilanthol producing plants, dissolved or suspended in the extraction/oil as described herein, using any of the applicable extraction methods or distillation and/or other means used to produce volatile essential oils from plants, respectively, as taught in the art.

Safety assessment studies of spilanthol are reported in the art: the acute toxicity of affinin was evaluated on ICR mice and the determined median lethal dose (LD50=113 mg/kg) was significantly higher than the amounts required to elicit anti-nociception. No mutagenic effects were observed by using the Ames test and antimutagenic effects of affinin were observed at 25 and 50 μg/ml. The cytotoxic effect of affinin was determined on human HEK293 kidney cells and the calculated mean inhibitory concentration (IC50) was 260 μg/ml, while the concentration used to observe biological effects was 100 μg/ml. No cytotoxic effects of affinin, which elicits a stimulatory effect on nitric oxide (NO) production in RAW 264.7 murine macrophages were observed at concentrations up to 40 μg/ml. Due to spilanthol's ability to be absorbed through the skin, it can enhance the ability of mycotoxins to penetrate the skin. So, it is important to make sure that formulations containing spilanthol are not contaminated with mycotoxins.

The toxicity tests described above and other toxicity tests of spilanthol are reported e.g., in Déciga-Campos et al., Drug Dev. Res., 73: 130-137, (2012); Déciga-Campos et al., Planta Med., 76: 665-670, (2010); Arriaga-Alba et al., Pharm. Biol., 51: 1035-1039, (2013); Gerbino et al., PLoS ONE, 11: e0156021, (2016); Wu et al., J. Agric. Food Chem., 56: 2341-2349, (2008).

The terms "spilanthol-containing extract" and "spilanthol-containing oil" encompass all variation of natural and enriched extracts and oils, respectively.

The amounts of any cannabinoid for example, CBD and/or THC, as well as the amounts of spilanthol in the composition may vary according to the intended use of the composition.

The compositions described herein facilitate co-administration of cannabinoids and spilanthol for use in any need that may benefit from synergistic, additive or potentiating therapeutic or non-therapeutic (e.g., cosmetic, personal hygiene) effect exerted by co-application of spilanthol and cannabinoids, such as, but not limited to, the diseases and conditions that are affected or are treatable by spilanthol consumption when applied alone or by cannabinoids consumption as described herein when applied alone.

Spilanthol and cannabinoids may be combined together and be provided as a stand-alone crude admixed composition. Alternatively, spilanthol and cannabinoids can be formulated e.g., as pharmaceutical compositions, cosmeceutical, cosmetic compositions, body care compositions, personal hygiene composition or food products, were they are mixed with suitable carriers, excipients and, optionally, further active agents.

The composition as described herein may be formulated as a single unit dose form essentially comprising a mixture of spilanthol and at least one cannabinoid either in their purified form and/or provided in extracts or essential oils as described herein.

Alternatively, or additionally, the composition described herein may be provided in two or more units of dosage form, at least one of which comprises spilanthol, spilanthol-containing extract and/or spilanthol-containing essential oils, and at least one dosage form comprising *cannabis* plant extract, *cannabis* plant essential oil, and/or at least one cannabinoid.

When formulated as separate dosage forms, spilanthol-containing plant material and *cannabis* or cannabinoids may be administered via the same route of administration, for example orally by eating or drinking. Additional, or alternatively, two or more different routes of administration may apply.

In some embodiments, the composition is an anti-colitis (inflammatory bowel disease) composition.

In some embodiments, the composition is an analgesic composition. In some embodiments, the composition is an anti-cancer composition.

The compositions described herein may also be formulated and provided as cosmeceuticals or as nutricosmetic compositions for combining beauty care with treating, mitigating, curing or preventing dermatological diseases and conditions such as, but not limited to, acne, eruption, burns, and cuts.

As used herein, the term "cosmeceutical" refers to a cosmetic product with bioactive ingredients purported to have medical or drug-like benefits. The "cosmeceutical" label applies only to products applied topically, such as creams, lotions and ointments. Products which are similar in perceived benefits but ingested orally are termed herein "nutricosmetics".

For example, the composition described herein may be used in the manufacture of anti-acne cream or paste.

Cosmetics and cosmeceuticals, also sometimes collectively referred to herein as "beauty products", are formulated in a form suitable, e.g., for topical application on an applied area, and may be used as anti-wrinkles, moisturizing creams, face masks, makeup, lipsticks and the like. A beauty product in accordance with some embodiments, may be in the form of a cream, an ointment, a paste, a gel, a lotion, a milk, an oil, a suspension, a solution, an aerosol, a spray, a foam, or a mousse.

For example, the composition described herein may be utilized in the manufacture of anti-wrinkle cream that can substitute for Botox in cosmetic applications or be added to anti-aging products. In another example, the composition described herein may be formulated and use as a skin penetration enhancer.

Composition as described herein may be formulated as body care products such as body lotions, soaps, body washes, moisturizers, self-tanners, hand cream, body scrub, sunscreen, bath products, or hygiene products such as toothpaste, soaps, shampoos, mouth wash, dental floss, deodorants, antiperspirants, shaving product such as shaving soap, gel or foam, and the like.

For example, the composition described herein may be used in the manufacture of toothpaste and be consumed as oral analgesic gel or paste.

The compositions described herein may also be added to food products, for example, to spices and be consumed by eating or drinking.

When formulated as pharmaceutical compositions or medicaments, cosmeceuticals or cosmetics, the compositions can be formulated by standard techniques or methods well-known in the art of pharmacy and cosmetics using at least one physiologically acceptable carrier or excipient. Suitable pharmaceutical carriers are described herein and in, e.g., "Remington's Pharmaceutical Sciences" by E. W. Martin.

As used herein a "pharmaceutical composition" refers to a preparation containing spilanthol and at least one cannabinoid as described herein (as active ingredient), or physiologically acceptable salts or prodrugs thereof, with other chemical components including but not limited to pharmaceutically suitable carriers, excipients, lubricants, buffering agents, antibacterial agents, bulking agents (e.g. mannitol), antioxidants (e.g., ascorbic acid or sodium bisulfite), anti-inflammatory agents, anti-viral agents, chemotherapeutic agents, anti-histamines and the like, as further described infra. The purpose of a pharmaceutical composition is to facilitate administration of the active agents to a subject. The term "active ingredient" refers to a compound, which is accountable for a desired biological effect.

As used herein, the term "pharmaceutically acceptable" means approved by a regulatory agency of the Federal or a state government or listed in the U.S. Pharmacopeia or other generally recognized pharmacopeia for use in animals, and more particularly in humans.

Herein, the phrase "pharmaceutically suitable carrier" refers to an approved carrier or a diluent that does not cause significant irritation to an organism and does not abrogate the biological activity and properties of a possible active agent.

Herein the term "excipient" refers to a non-active substance added to a pharmaceutical or to a cosmetic composition to further facilitate processes and administration of the active ingredients. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions, cosmeceutical and cosmetic compositions for use in accordance with the present invention thus may be formulated in conventional manner using at least one pharmaceutically acceptable carriers or cosmetically acceptable carriers comprising excipients and auxiliaries, which facilitate processing of the compounds into preparations which can be used pharmaceutically or cosmetically. Proper formulation is dependent upon the route of administration chosen.

For pharmaceutical compositions, the dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

Since the present teachings relate to the production of compositions which are endowed with pharmaceutical activities and/or cosmetic activities, the composition may further comprise other active agents such as pharmaceutical agents, plant extracts with medical and/or cosmetic use, essential oils, serums, proteins, vitamins and the like.

In some embodiments, the pharmaceutical agent is a phytochemical, namely, a chemical compound produced by plants through primary or secondary metabolism. Phytochemicals generally have biological activity in the plant host and play a role in plant growth or defense against competitors, pathogens, or predators. Examples of such phytochemicals include, but are not limited to, terpenoids, flavonoids, tannins, phenols, saponins, polyphenols, heterosides, alkamides and alkaloids.

Examples of medicinal plants from which additional active agents may be extracted and added to the compositions described herein include, but are not limited to, *Salvia sclarea, Echinacea purpurea*, extracts from citruses. Examples of active ingredients include, but are not limited to, heterosides: anthraquinones, cardiac glycosides, cyanogenics; coumarins flavonoids, phenols, ranunculosides, saponosides, sulphurides; polyphenols: phenolic acids, coumarins, flavonoids, lignans, tannins, quinine; and terpenoids: essential oils, iridoids, lactones, diterpenes, saponins.

In some embodiments, the active agent is not naturally present in (i.e., endogenous to) the *cannabis* trichome or *cannabis* oil nor the spilanthol-containing plant.

In some embodiments, the pharmaceutical agent is an antibacterial agent, an antioxidant (e.g., ascorbic acid or sodium bisulfite), an anti-inflammatory agent, an anti-viral agent, an antifungal agent, an anti-microbial agent, a chemotherapeutic agent, an apoptosis inducing agent, an anti-diarrheal agent, an anti-histamine, an analgesic agent, and/or an anti-depressant agent.

The composition may comprise from about 0.1% to about 10% by weight or by volume of pharmaceutical or otherwise active agent, for example, 0.1-1.0%, 0.1-0.9%, 0.1-0.8%, 0.1-0.7%, 0.1-0.6%, 0.1-0.5%, 0.1-0.3%, 0.1-0.2%, 1-5%, 2-5%, 2-6%, 3-8%, 4.0-9%, 5-8%, 6-9%, 5-10%, 7-10%, or 9-10%, by weight or by volume.

For example, a composition in accordance with the invention may be formulated as a psoriasis cream that contains CBD, spilanthol, and about 3% salicylic acid as the pharmaceutical agent.

The compositions described herein may comprise at least one essential oil which is not necessarily originating from a *cannabis* plant or an spilanthol-producing plant. Such essential oils are added to the compositions to provide properties such as improved palatability. Essential oils can also provide antioxidant and preservative properties to the compositions. The identity and amount of the essential oil(s) added can depend in part on factors including the strain of *cannabis* and/or the spilanthol-producing plant that has been extracted, and the desired organoleptic properties.

In general, the amount of total essential oils added to a composition will range from about 0.01% (w/w) to about 10% (w/w) or more. The total amount of essential oils added can range, for example, from about 0.01% (w/w) to about 0.5% (w/w), or from about 0.5% (w/w) to about 1% (w/w), or from about 1% (w/w) to about 2% (w/w), or from about 2% (w/w) to about 3% (w/w), or from about 3% (w/w) to about 4% (w/w), or from about 4% (w/w) to about 5% (w/w), or from about 5% (w/w) to about 6% (w/w), or from about 6% (w/w) to about 7% (w/w), or from about 7% (w/w) to about 8% (w/w), or from about 8% (w/w) to about 9% (w/w), or from about 9% (w/w) to about 10% (w/w).

For example, the amount of total essential oils added may about 0.05%, about 1.7%, or about 2.5% (w/w). The % (w/w) values indicated are based on the amount of essential oil added to the total amounts of other ingredients and constituents of the composition. Examples of essential oils include, but are not limited to, bergamot essential oil, blood orange essential oil, sweet orange essential oil, neroli essential oil, peppermint essential oil, lavender essential oil, lemongrass essential oil, vanilla essential oil and spearmint essential oil. Other essential that can be added to the compositions described herein are disclosed in U.S. Patent Publication No. 2016/0346339 hereby incorporated by reference in its entirety.

In some embodiments, additional carrier oils are added to the compositions as described herein. Examples of carrier oils include, but are not limited to: almond oil; aloe vera oil; apricot kernel oil; avocado oil; argan oil; calendula oil; carrot seed oil; castor oil; coconut oil; evening primrose oil; fish oils and oils rich in omega-3 fatty acids (e.g., algae, krill, flaxseed); grape seed oil; hazelnut oil; hemp seed oil; jojoba oil; macadamia oil; olive oil; raspberry seed oil; sesame oil; sunflower oil; walnut oil; wheatgerm oil; and combinations thereof. In some embodiments, the carrier oil is hemp seed oil.

When added, a carrier oil will typically be present in an amount ranging from about 1% (w/w) to about 95% (w/w).

The composition described herein may comprise vitamins, such as, but not limited to, vitamin A, vitamin B, Vitamin C, vitamin D, vitamin E and vitamin K.

It will be appreciated that other ingredients may be added to the composition. Such ingredients may include, but are not limited to, probiotics, coloring agents, emulsifiers, herbal extracts with medical uses, flavors, flower essences and proteins.

The amount of *cannabis* extract or *cannabis* oil or any specific cannabinoid, either purified or synthetic, in the composition may vary from 0.1% to 99.9% in accordance with the intend use of the composition. Likewise, the amount of spilanthol-containing extract or spilanthol-containing essential oil or purified or synthetic spilanthol in the composition may vary from 0.1% to 99.9% in accordance with the intended use of the composition.

In some embodiments, the *cannabis* extract or *cannabis* oil or any specific cannabinoid is present in the composition at an amount of at least 5%, at least 10%, at least 20%, at least 30%, at least 40%, at least 50%, at least 60%, at least 65%, at least 70%, at least 80%, at least 90%, at least 95%, weight percent.

In some embodiments, the composition comprises 50-95%, 60-95%, 70-95%, 80-95%, 90-95%, 50-90%, 60-90%, 70-90%, 80-90%, 60-80%, 60-70%, 65-75%, of *cannabis* extract and/or *cannabis* oil and/or any specific cannabinoid, either purified or synthetic.

In some embodiments, the composition comprises 5-50%, 5-45%, 5-40%, 5-35%, 5-30%, 5-25%, 5-20%, 5-15%, 5-12%, 5-10%, 5-8%, 5-7%, 5-6%, 10-45%, 10-40%, 10-35%, 15-30%, 15-25%, 15-20%, 20-50%, 20-40%, 25-40%, 30-45%, 35-40%, or 40-50% of *cannabis* extract and/or *cannabis* oil and/or any specific cannabinoid, either purified or synthetic.

In some embodiments, the *cannabis* oil or *cannabis* extract or any cannabinoid may be presents in the composition at an amount not exceeding 5%, 4%, 3%, 2%, 1%, 0.9%, 0.8%, 0.7%, 0.5%, 0.4%, 0.3% or 0.2%.

In some embodiments, the composition comprises 0.1-5%, 0.1-4.5%, 0.1-4.0%, 0.1-3.5%, 0.1-3.0%, 0.1-2.5%, 0.1-2.0%, 0.1-1.5%, 0.1-1.2%, 0.1-1.0%, 0.1-0.8%, 0.1-0.5%, 0.1-0.4%, 0.1-0.3%, or 0.1-0.2% of *cannabis* extract and/or *cannabis* oil and/or any specific cannabinoid, either purified or synthetic.

In some embodiments, the spilanthol-containing extract or pure spilanthol is present in the composition at an amount of at least 50%, at least 60%, at least 65%, at least 70%, at least 80%, at least 90%, at least 95%.

In specific embodiments, the composition comprises 50-99.9%, 60-99.9%, 70-99.9%, 80-99%, 90-99.9%, 95-99.9%, 96-99.9%, 97-99.9%, 98-99.9%, 50-90%, 60-90%, 70-90%, 80-90%, 60-80%, 60-70%, 65-75%, 60-95%, 70-95%, 80-95%, 90-95%, 95-99%, 97-99%, or 98-99% of spilanthol-containing extract or pure spilanthol.

In some embodiments, the spilanthol-containing extract or pure spilanthol is present in the composition at an amount not exceeding 5%, 4%, 3%, 2%, 1%, 0.9%, 0.8%, 0.7%, 0.5%, 0.4%, 0.3% or 0.2%.

In some embodiments, the composition comprises 0.1-5%, 0.1-4.5%, 0.1-4.0%, 0.1-3.5%, 0.1-3.0%, 0.1-2.5%, 0.1-2.0%, 0.1-1.5%, 0.1-1.2%, 0.1-1.0%, 0.1-0.8%, 0.1-0.5%, 0.1-0.4%, 0.1-0.3%, or 0.1-0.2% of spilanthol-containing extract or pure spilanthol.

In some embodiments, the composition comprises 5-50%, 5-45%, 5-40%, 5-35%, 5-30%, 5-25%, 5-20%, 5-15%, 5-12%, 5-10%, 5-8%, 5-7%, 5-6%, 10-45%, 10-40%, 10-35%, 15-30%, 15-25%, 15-20%, 20-50%, 20-40%, 25-40%, 30-45%, 35-40%, or 40-50% of spilanthol-containing extract or pure spilanthol.

In exemplary embodiments, the composition comprises 10-600 mg/gr, 10-200 mg/gr, 10-100 mg/gr, 50-100 mg/gr, THC and/or CBD.

In exemplary embodiments, the composition comprises 10-600 mg/g, 10-200 mg/gr, 10-100 mg/gr, 50-100 mg/gr, spilanthol.

Of note, water can be added to the composition in order to dilute the active ingredients. According to specific embodiments, the water present does not exceed 50%, 45%, 40%, 35%, 30%, 25%, 20%, 15% or 10%.

The combination composition comprising cannabidiol (CBD) and spilanthol was assessed in preclinical studies in the treatment of inflammatory bowel disease (IBD) was assessed in mice in the preclinical model of Dextran Sodium Sulphate (DSS) induced colitis (see Example 2 and FIGS. 1-6).

The CBD/spilanthol ratios of 10:1 and 5:1 were used in the study.

Based on the study results, the 5:1 seems to be more effective.

In an embodiment, there are provided compositions comprising CBD and spilanthol, in a w/w ratio ranging from about 1/1 to about 5/1, from about 5/1 to about 10:1, from about 10/1 to about 20/1, from about 20/1 to about 30/1, from about 30/1 to about 40/1, from about 40/1 to about 50/1.

In another embodiment, there are provided compositions comprising CBD and spilanthol, in a w/w ratio ranging about 50/1 to about 60/1, from about 60/1 toto about 70:1, from about 70/1 to about 80/1, from about 80/1 to about 90/1, from about 90/1 to about 100/1.

The spilanthol and CBD dosages used in the above preclinical study in mice were 50 mg/kg CBD and 10 mg/kg spilanthol.

For a 70 kg human, this would be equivalent to 500 mg CBD and 100 mg spilanthol per day (multiplying by 70 but and dividing by 7 because the mice to human conversion).

Based on the above, the equivalent daily human doses for colitis treatment would be 500 mg CBD and 100 mg spilanthol.

Of course, dosage ranging studies must be carried out on various dosages.

In some embodiments, there are provided fixed-dose combination compositions comprising 150 mg CBD and 30 mg spilanthol (5:1 ratio), 250 mg CBD and 50 mg spilanthol (5:1 ratio), 100 mg CBD and 10 mg spilanthol (10:1 ratio) and 500 mg CBD and 25 mg spilanthol (20:1 ratio).

In some other embodiments, there are provided combination compositions comprising 250 mg CBD and 50 mg spilanthol (5:1 ratio), 500 mg CBD and 100 mg spilanthol (5:1 ratio), 750 mg CBD and 75 mg spilanthol (10:1 ratio) and 1000 mg CBD and 50 mg spilanthol (20:1 ratio).

In some other embodiments, there are provided combination compositions comprising 10 mg CBD and 2 mg spilanthol (5:1 ratio), 20 mg CBD and 4 mg spilanthol (5:1 ratio), 50 mg CBD and 5 mg spilanthol (10:1 ratio) and 100 mg CBD and 5 mg spilanthol (20:1 ratio).

According to some embodiments, there is provided a regimen of administration comprising the administration to a patient in need thereof of one of the above combination compositions comprising spilanthol and at least one cannabinoid once twice, twice or three times daily, during a period of 1-10 days, 1-20 days or 1-30 days or until the medical condition subsides.

In some embodiments, the combination compositions of this invention comprise from about 5 mg to about 500 mg CBD.

In some embodiments, the combination compositions of this invention comprise from about 1 mg to about 100 mg CBD.

In an exemplary embodiment, the composition comprises:
50-99.9% *cannabis* oil or *cannabis* extract;
1-45% spilanthol-containing extract; and optionally
0.1-2% pharmaceutical active agent.

In accordance with this particular embodiment, the composition is prepared by mixing the *cannabis* oil or *cannabis* extract with a spilanthol-containing extract, both of which are optionally diluted in oil or emulsifier, with the pharmaceutical. Other ingredients such as described herein can be added.

In an exemplary embodiment, *cannabis* oil and/or *cannabis* hemp flowers in the form of a cake or powder are added to liquid mixture containing spilanthol-containing extract. The composition is mixed by shaking. Finally, other ingredients such as natural coloring agents are added. The components are mixed until reaching a homogeneous composition. Typically, mixing is done while heating (e.g., to 75° C.).

Of note, all percentages indicated herein refer to w/w, v/v, v/w or w/v.

The composition described herein can be formulated for administration by any suitable route, including, but not limited to, orally, topically, nasally, rectally, vaginally, pulmonary, parenterally (e.g., intravenously, subcutaneously, intramuscularly, etc.), and any combinations thereof. In some embodiments, the composition is diluted in a liquid, e.g., a carrier oil. The most suitable route of administration in any given case will depend in part on the condition being treated as well as the response of the subject to the particular route of treatment.

In some embodiments, compositions as described herein are administered via a vaporizer or like device as described, for example, in U.S. Pat. No. 8,915,254; U.S. Patent Application Publication No. 2014/0060552; U.S. Pat. No. 8,488,952; and U.S. Patent Application Publication No. 2015/0040926.

Compositions for pulmonary administration also include, but are not limited to, dry powder compositions consisting of the powder of a *cannabis* extract, cannabinoids, spilanthol or spilanthol-containing extract described herein, and the powder of a suitable carrier and/or lubricant. The compositions for pulmonary administration can be inhaled from any suitable dry powder inhaler device known to a person skilled in the art. In certain instances, the compositions may be conveniently delivered in the form of an aerosol spray from pressurized packs or a nebulizer, with the use of a suitable propellant, for example, dichlorodifluoromethane, trichlorofluoromethane, dichlorotetrafluoroethane, carbon dioxide, or other suitable gas.

In the case of a pressurized aerosol, the dosage unit can be determined by providing a valve to deliver a metered amount. Capsules and cartridges of, for example, gelatin for use in an inhaler or insufflator can be formulated containing a powder mix of the ingredients of the composition and a suitable powder base, for example, lactose or starch.

For oral administration, a pharmaceutical composition or a medicament can take the form of, e.g., a tablet or a capsule prepared by conventional means with a pharmaceutically acceptable excipient. Preferred are tablets and gelatin capsules comprising the active ingredient(s), together with (a) diluents or fillers, e.g., lactose, dextrose, sucrose, mannitol, maltodextrin, lecithin, agarose, xanthan gum, guar gum, sorbitol, cellulose (e.g., ethyl cellulose, microcrystalline cellulose), glycine, pectin, polyacrylates and/or calcium hydrogen phosphate, calcium sulfate, (b) lubricants, e.g., silica, anhydrous colloidal silica, talcum, stearic acid, its magnesium or calcium salt (e.g., magnesium stearate or calcium stearate), metallic stearates, colloidal silicon dioxide, hydrogenated vegetable oil, corn starch, sodium benzoate, sodium acetate and/or polyethylene glycol (PEG); for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium or potassium salt, or effervescent mixtures; (e) wetting agents, e.g., sodium lauryl sulfate, and/or (f) absorbents, colorants, flavors and sweeteners. Tablets can be either uncoated or coated according to methods known in the art.

The excipients described herein can also be used for preparation of buccal dosage forms and sublingual dosage forms (e.g., films and lozenges) as described, for example, in U.S. Pat. Nos. 5,981,552 and 8,475,832. Formulation in chewing gums as described, for example, in U.S. Pat. No. 8,722,022, is also contemplated.

Further preparations for oral administration can take the form of, for example, solutions, syrups, suspensions, and toothpastes. Liquid preparations for oral administration can be prepared by conventional means with pharmaceutically acceptable additives, for example, suspending agents, for example, sorbitol syrup, cellulose derivatives, or hydrogenated edible fats; emulsifying agents, for example, lecithin, xanthan gum, or acacia; non-aqueous vehicles, for example, almond oil, sesame oil, hemp seed oil, fish oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate.

Typical formulations for topical administration include creams, ointments, sprays, lotions, hydrocolloid dressings, and patches, as well as eye drops, ear drops, and deodorants. The compositions described herein can be administered via transdermal patches as described, for example, in U.S. Patent Application Publication No. 2015/0126595 and U.S. Pat. No. 8,449,908.

Formulation for rectal or vaginal administration is also contemplated. The composition can be formulated, for example, as suppositories containing conventional suppository bases such as cocoa butter and other glycerides as described in U.S. Pat. Nos. 5,508,037 and 4,933,363. Compositions can contain other solidifying agents such as shea butter, beeswax, kokum butter, mango butter, illipe butter, tamanu butter, carnauba wax, emulsifying wax, soy wax, castor wax, rice bran wax, and candelila wax. Compositions can further include clays (e.g., Bentonite, French green clays, Fuller's earth, Rhassoul clay, white kaolin clay) and salts (e.g., sea salt, Himalayan pink salt, and magnesium salts such as Epsom salt).

The compositions set forth herein can be formulated for parenteral administration by injection, for example, by bolus injection or continuous infusion. Formulations for injection can be presented in unit dosage form, for example, in ampoules or in multi-dose containers, optionally with an added preservative. Injectable compositions are preferably aqueous isotonic solutions or suspensions, and suppositories are preferably prepared from fatty emulsions or suspensions.

The compositions may be sterilized and/or contain adjuvants, such as preserving, stabilizing, wetting or emulsifying agents, solution promoters, salts for regulating the osmotic pressure, buffers, and/or other ingredients.

Alternatively, the compositions can be in powder form for reconstitution with a suitable vehicle, for example, a carrier oil, before use. In addition, the compositions may also contain other therapeutic agents or substances.

The compositions can be prepared according to conventional mixing, granulating, and/or coating methods, and contain from about 0.1 to about 75%, preferably from about 1 to about 50%, of the total active ingredients.

In general, subjects receiving a composition orally are administered amounts ranging from about 1 to about 2000 mg of *cannabis* oil or *cannabis* extract, from about 1 to about 500 mg of pure spilanthol or from about 10 to about 2000 mg of extract thereof. A small dose ranging from about 1 to about 20 mg of the whole composition can typically be administered orally when treatment is initiated, and the dose can be increased (e.g., doubled) over a period of days or weeks until the maximum dose is reached. Pharmaceutical compositions may be administered for example, during 28 days.

The pharmaceutical compositions, cosmeceuticals, cosmetic compositions, food products, body care products, personal hygiene products and the like described hereinabove are packaged in a packaging material and identified in print, in or on the packaging material, for use in the relevant application.

Methods of Treatment

According to a further aspect of the invention, there is provided a method of treating, curing or alleviating a disease, disorder or medical condition which is treatable and/or alleviated by a combination composition of at least one cannabinoid and spilanthol, the method comprising co-administering to a subject in need thereof effective amounts of spilanthol and of at least one cannabinoid and/or *cannabis* extract, thereby treating, curing or alleviating the disease, disorder or medical condition.

In some embodiments, the effective amount is a therapeutically effective amount of spilanthol and/or of at least one cannabinoid or of the *cannabis* extract, namely an amount which will cure, treat, mitigate or prevent disease or will affect the structure or function of the human body.

In some embodiments, co-administration of spilanthol and at least one cannabinoid and/or *cannabis* extract results in an additive effect while treating or alleviating a disease or condition effected or treatable both by spilanthol and cannabinoids/*cannabis*.

In some embodiments, co-administration of spilanthol and at least one cannabinoid such as CBD and/or *cannabis* extract results in a potentiating effect while treating or alleviating a disease or condition effected or treatable both by spilanthol and cannabinoids/*cannabis*. Namely, one active agent, e.g., spilanthol potentiates the therapeutic effect of the other active agent, e.g., at least one cannabinoid and/or cannabinoids potentiate the therapeutic effect of spilanthol.

Embodiments featuring "co-administration" of spilanthol and cannabinoids/*cannabis* include embodiments wherein spilanthol and at least one cannabinoid, *cannabis* extract and/or *cannabis* essential oil are administered or consumed simultaneously, and embodiments of consecutive administration, wherein one active agent, e.g., spilanthol, spilanthol-containing extract or spilanthol-containing essential oil is administered followed or preceded by a second active agent e.g., at least one cannabinoids, *cannabis* extract or *cannabis* essential oil.

The at least one cannabinoid may be administered or consumed together at the same time, or, alternatively, they may be administered or consumed separately according to a predetermined regimen, for example, before, together with and/or after administration or consumption of spilanthol.

Co-administration of spilanthol at least one cannabinoid and/or *cannabis* may be carried out by providing to a subject in need thereof a composition as described herein formulated as a single unit dose form essentially comprising spilanthol, spilanthol-containing extract and/or spilanthol-containing essential oils, and at least one cannabinoid, *cannabis* extract and/or *cannabis* oil.

Alternatively, or additionally, co-administration of spilanthol and at least one cannabinoid and/or *cannabis* is carried out by providing to a subject in need thereof two or more units of dosage form, at least one of which comprises spilanthol, spilanthol-containing extract and/or spilanthol-containing essential oils, and at least one dosage form comprises *cannabis* extract, *cannabis* essential oil, and/or at least one cannabinoid.

Inflammatory Bowel Disease (IBD) Treatment with the Combination Compositions of this Invention The efficacy of CBD, spilanthol and a combination of CBD and spilanthol in the treatment of inflammatory bowel disease (IBD) was assessed in a preclinical study in mice (see Example 2 and FIGS. 1-6). The preclinical model of choice was Dextran Sodium Sulphate (DSS) induced colitis.

Mice were divided into 4 study groups (10 mice in each group): 1. Vehicle treatment group; 2. CBD 50 mg/kg treatment group; 3. Spilanthol 10 mg/kg treatment group; and 4. CBD 50 mg/kg+Spilanthol 10 mg/kg combination treatment group (herein "test combination group").

Study Readouts

The following 3 parameters were measured in the study as indicators for assessing the amelioration and the therapeutic efficacy of the different treatments: 1. Changes in body weight, 2. Colon TNFα levels as measured by ELISA kits (R&D Systems, USA), 3. Total length of colon from cecum to anus, as measured by a blinded veterinary doctor.

Study Results

Figure 2:
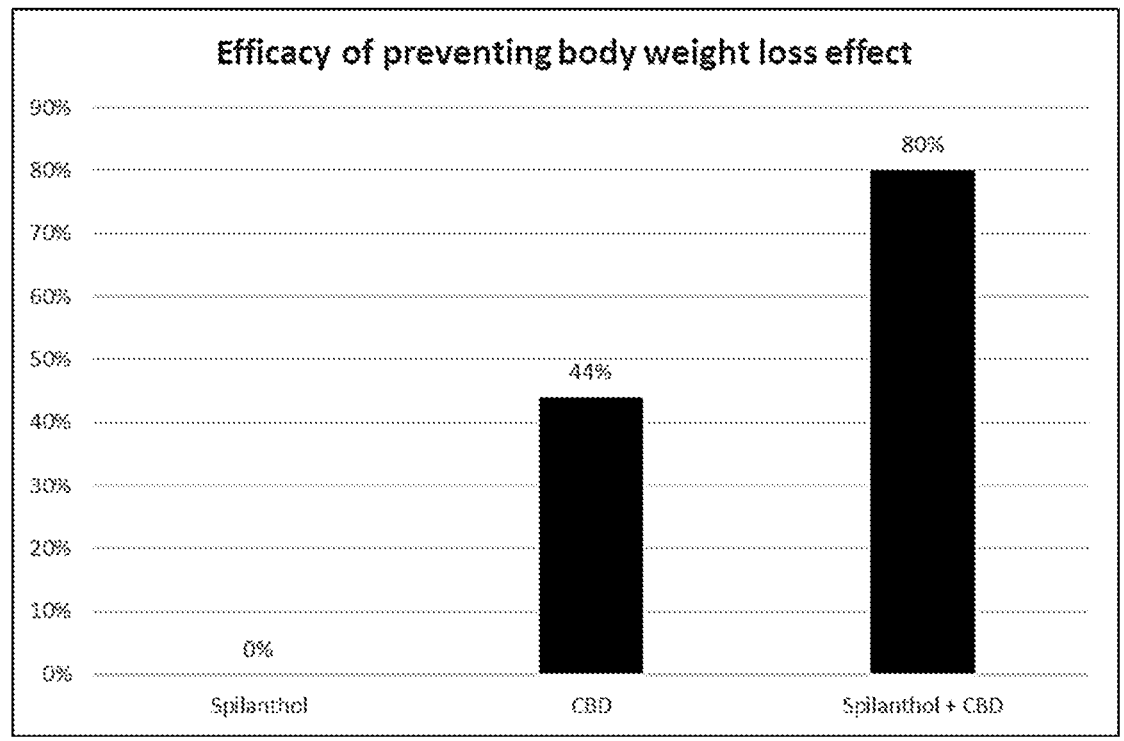
FIG. 2 depicts the efficacy of preventing the body weight loss effect in mice, after treatment with spilanthol, CBD or spilanthol+CBD.

Body Weight Loss:

Mice of the vehicle treatment group lost on average 14.6% of baseline body weight as measured on day 9 of the study. The combination treatment group lost only 2.9% of body weight on average as measured on day 9 of the study (FIG. 1). While the Spilanthol treatment alone did not show any efficacy signs in improving the body weight loss as compared to vehicle group (0% improvement in outcome) and the CBD treatment alone was able to prevent 44% of the weight loss effect caused by the DSS induced colitis itself, the combination therapy demonstrated an 80% prevention of weight loss (FIG. 2). This result demonstrates a clear synergistic therapeutic effect of the Spilanthol and CBD when administered together as a combination therapy, since the ameliorating therapeutic effect of the combination treatment is stronger than the sum of the effects of the two active agents when administered separately (80%>0%+44%).

Figure 3:
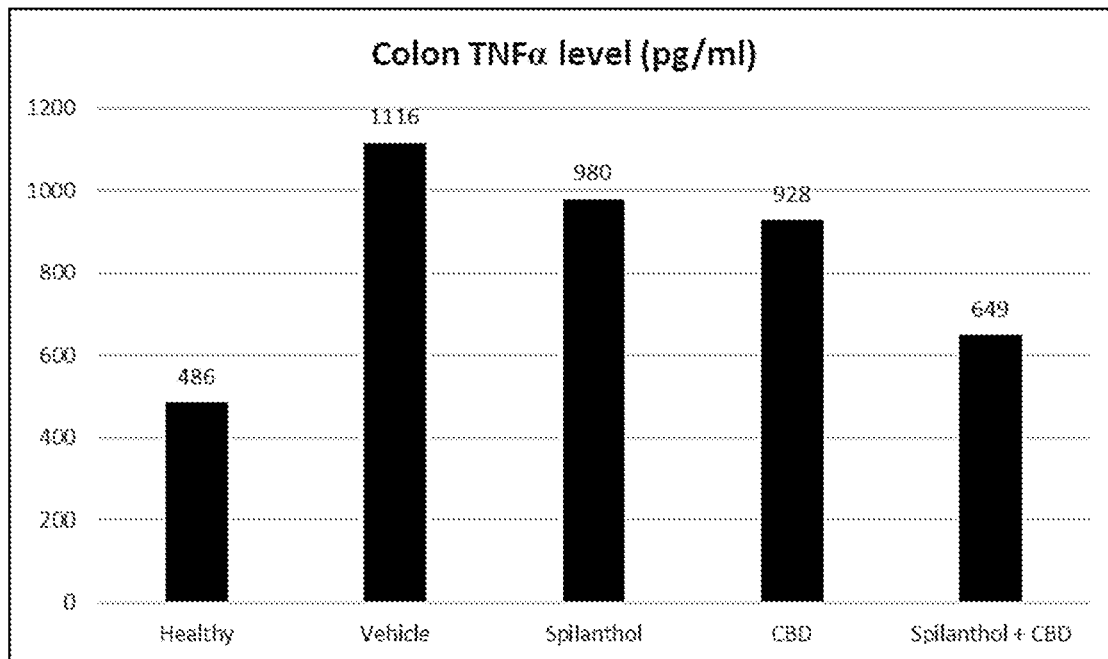
FIG. 3 depicts the colon TNFα level (pg/ml) in healthy mice as compared to mice treated with vehicle, spilanthol, CBD or spilanthol+CBD.
Figure 4:
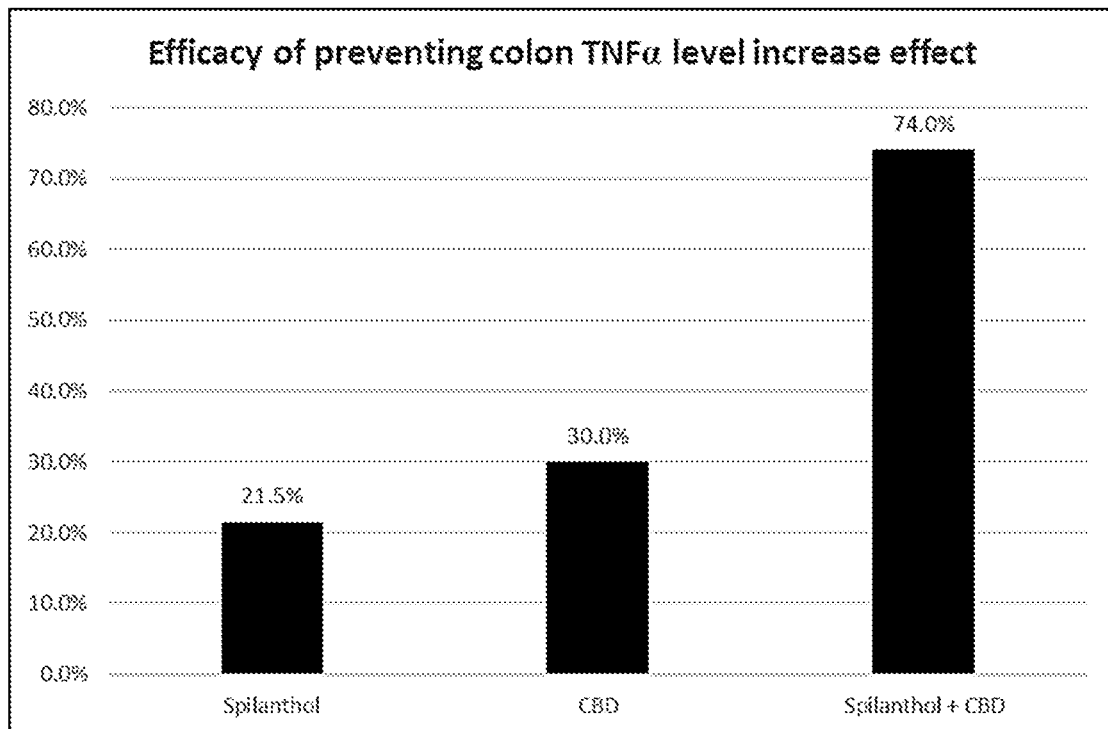
FIG. 4 depicts the efficacy of preventing colon TNFα level increase effect in mice treated with spilanthol, CBD or spilanthol+CBD.

Colon's Tnfα Levels:

The average colon's TNFα level in the healthy mice group (unconditioned by DSS) was measured as 486 pg/ml. The average colon TNFα level in the vehicle treatment group was measured as 1,116 pg/ml, representing a 630 pg/ml increase of TNFα levels as a result of conditioning by DSS as compared to natural baseline levels—a 130% increase, which represents the increase in colon inflammatory factors concentration as a result of the DSS insult. In the single active agent arms, the average colon TNFα level as measured in the Spilanthol treatment group was 980 pg/ml (representing a 101% increase from baseline) and 928 pg/ml were measured in the CBD group (91% increase). However, the average level of colon TNFα in the combination group was measured as 649 pg/ml—an increase of only 33.5% over baseline levels (FIG. 3). While the Spilanthol treatment alone was able to reduce the TNFα level by 136 pg/ml comparing to vehicle (21.5% reduction of effect) and the CBD treatment alone was able reduce it by 188 pg/ml (30% reduction), the combination therapy demonstrated an ability to reduce the colon TNFα level by 467 pg/ml comparing to vehicle, which represents a 74% reduction in the TNFα increase effect (FIG. 4). This result further demonstrates a synergistic therapeutic effect of the Spilanthol and CBD when administered together as a combination therapy, since the ameliorating therapeutic effect of the combination treatment is stronger than the sum of the effects of the two constituents when administered separately (74%>21.5%+30%).

Figure 5:
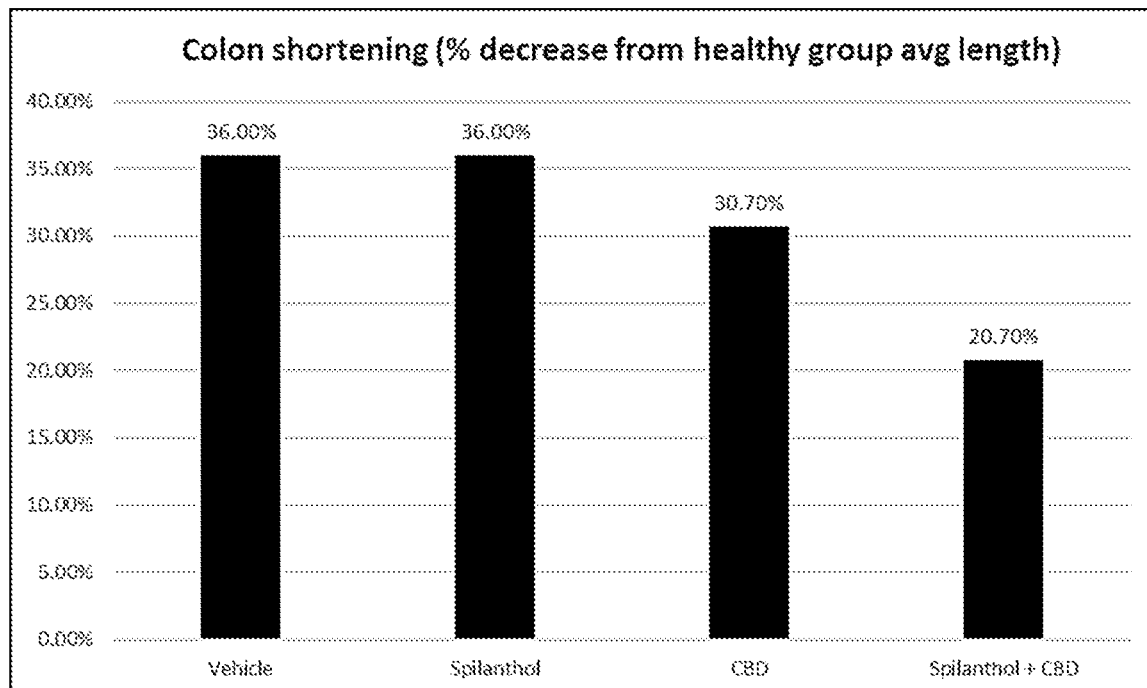
FIG. 5 depicts the colon shortening (% decrease as compared to healthy group average length.
Figure 6:
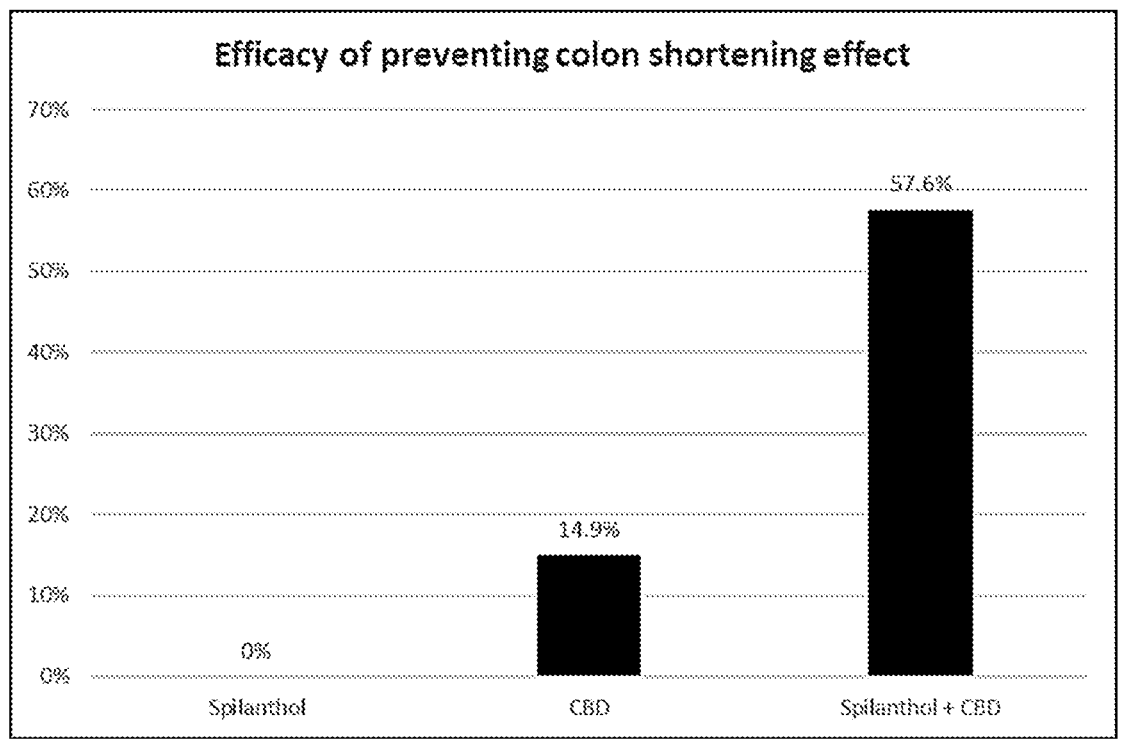
FIG. 6 depicts the efficacy of preventing the colon shortening effect in mice treated with spilanthol, CBD or spilanthol+CBD.

Total Length of Colon from Cecum to Anus:

The average colon length as measured in the healthy mice group (unconditioned by DSS) was 7.6 cm. The average colon length in the vehicle treatment group was measured as 4.9 cm, representing a 2.76 cm decrease of colon length as a result of conditioning by DSS as compared to natural baseline lengths—a 36% decrease. The average colon length as measured in the Spilanthol treatment group was 4.9 cm (representing a 36% decrease from baseline—the same like vehicle) and an average colon length of 5.31 cm was measured in the CBD group (a 30.7% decrease). However, the average colon length as measured in the combination treatment group was 6.07 cm—representing a decrease of only 20.7% from average baseline length (FIG. 5). In other words, while the Spilanthol treatment alone didn't show any efficacy in reducing the colon shortening effect at all (0% improvement in outcome) and the CBD treatment alone was able to reduce the effect by 0.41 cm (14.9% improvement in outcome), the combination therapy demonstrated an ability to reduce the colon shortening effect by 1.59 cm, which represents a 57.6% improvement in outcome (FIG. 6). This result again further demonstrates a synergistic therapeutic effect of the Spilanthol and CBD when administered together as a combination therapy, since the ameliorating therapeutic effect of the combination treatment is stronger than the sum of the effects of the two constituents when administered separately (57.6%>0%+14.9%).

Conclusions of the Preclinical Study of the CBD+Spilanthol Combination

Three different parameters that measure the potential therapeutic effects of spilanthol alone, CBD alone and the combination thereof were examined for the amelioration of the deleterious effects caused by a DSS induced colitis condition in mice. All three examined parameters showed a clear synergistic effect between the two active agents, with the combined therapy achieving better results than the sum of the improvement results achieved by any of them when administered separately, with a strong statistical significance. This result demonstrates the potential superior and synergistic therapeutic efficacy that can be achieved by using these two active agents spilanthol and CBD as a combined therapy as compared to each of them separately.

Other diseases and conditions treatable and/or alleviated by co-administration of spilanthol (e.g., isolated and purified from plant material or chemically synthesized), spilanthol-containing extract, and/or spilanthol-containing essential oil, and cannabinoids and/or *cannabis* and/or *cannabis* extract and/or *cannabis* essential oil, include, but are not limited to, a gastro-enterologic, an inflammatory, an autoimmune, a neurodegenerative, an oncologic, a cardiovascular, or an infectious (e.g., viral, bacterial, fungal) disease or disorder.

Non-limiting examples of medical conditions treatable or alleviated by the composition described herein include nausea, appetite loss and pain associated with cancer and chemotherapy; nausea, appetite lose, pain and wasting associated with AIDS; toothache; arthritis and rheumatism; glaucoma; scurvy; migraine; muscle spasticity associated e.g., with multiple sclerosis and paralysis; alcohol and narcotics withdrawal; stress; depression; asthma; neurological disorders such as Tourette syndrome, Cervical dystonia or epileptic seizures; dementia; dysmenorrhea; anxiety disorders; diabetes; diarrhea; neuropathic pain; chronic pain; autoimmune diseases; skin diseases such as psoriasis, dermatitis and swimmer's eczema; neurodegeneration and neurodegenerative disorders such as Alzheimer's disease, Huntington disease and Parkinson's disease; Lyme disease; post-traumatic stress disorder; inflammation such as liver inflammation; mental diseases such as schizophrenia; post-traumatic stress disorder (PTSD) and pain associated therewith; malaria; vasoconstriction, allergy; edema colitis; heart diseases; painful spasms; fibromyalgia and pain associated therewith; sexual disfunction; and other medical conditions described throughout the specification.

In some embodiments, the condition treated by co-administration of spilanthol, spilanthol-containing extract and/or spilanthol-containing essential oil, and at least one cannabinoid and/or *cannabis* extract and/or *cannabis* oil, is sepsis, a life-threatening condition that arises when the body's response to infection causes injury to its own tissues and organs.

In some embodiments, the disease or condition treated by co-administration of spilanthol and at least one cannabinoid is necrotizing soft tissue infections (NSTI).

NSTIs are aggressive severe soft tissue infections that cause rapid and widespread infection and necrosis of the skin and soft tissues and are highly lethal. NSTIs include necrotizing cellulitis, adipositis, fasciitis and myositis/myonecrosis and have significant potential for extensive soft tissue and limb loss. Co-administration of spilanthol and cannabinoids and/or *cannabis* (e.g., *cannabis* extract or *cannabis* oil) optionally together with surgical debridement and/or early appropriate antibiotic treatment can provide a successful outcome and clinical cure of NSTI.

In some embodiments, the disease or condition treated by co-administration of spilanthol and at least one cannabinoid is acute and chronic pancreatitis.

In some embodiments, the condition treated by co-administration of spilanthol and at least one cannabinoid and/or *cannabis* (e.g., *cannabis* extract or *cannabis* oil) is opioid addiction.

Opioids are a class of drugs that include the illicit drug heroin as well as the licit prescription pain relievers oxycodone, hydrocodone, codeine, morphine, fentanyl and others. Opioids are chemically related and interact with opioid receptors on nerve cells in the brain and nervous system to produce pleasurable effects and relieve pain. Addiction is a primary, chronic and relapsing brain disease characterized by an individual pathologically pursuing reward and/or relief by substance use and other behaviors. It is estimated that 23% of individuals who use heroin develop opioid addiction. Co-administration of spilanthol (e.g., purified form plant material or chemically synthesized), spilanthol-containing extract or essential oil, and cannabinoids and/or *cannabis* (e.g., *cannabis* extract or *cannabis* oil) can provide a significant relief in addiction.

In some embodiments, the disease or condition treated by co-administration of spilanthol and at least one cannabinoid is inflammatory bowel disease (IBD).

Inflammatory bowel disease represents a group of intestinal disorders that cause prolonged inflammation of the digestive tract. Many diseases are included in this IBD umbrella term. The two most common diseases are ulcerative colitis and Crohn's disease. Crohn's disease can cause inflammation in any part of the digestive tract. However, it mostly affects the tail end of the small intestine. Ulcerative colitis involves inflammation of the large intestine. Co-administration of spilanthol (e.g., isolated and purified from plant material or chemically synthesized), spilanthol-containing extract and/or spilanthol-containing essential oil, and cannabinoids and/or *cannabis* (e.g., *cannabis* extract or *cannabis* oil) can e.g., alleviate at least one symptom of IBD such as diarrhea, stomach pain, bleeding ulcers and weight loss.

In some embodiments, the disease or condition treated by co-administration of spilanthol and at least one cannabinoid irritable bowel syndrome (IBS).

Irritable bowel syndrome (IBS) is a common disorder that affects the large intestine (colon), with worldwide prevalence rates estimated in the range of 10%-15% of the population. Irritable bowel syndrome commonly causes cramping, abdominal pain, bloating, gas, alternating periods of persistent diarrhea or constipation and mucus in the stool. IBS is a chronic condition, however, unlike ulcerative colitis and Crohn's disease, which are forms of inflammatory bowel disease, IBS doesn't cause changes in bowel tissue or increases the risk of colorectal cancer. Co-administration of spilanthol (e.g., purified form plant material or chemically synthesized), spilanthol-containing extract and/or spilanthol-containing essential oil, and cannabinoids and/or *cannabis* (e.g., *cannabis* extract or *cannabis* oil) has shown a strong synergistic effect in the treatment of IBS, e.g., in alleviating at least one symptom of IBS such as diarrhea, abdominal pain, bloating, or gas.

For example, a composition comprising spilanthol and at least one cannabinoid such as CBD, can be formulated as a nutraceutical, a food supplement or wellness product for treating IBS. Such a product may be a generally regarded as safe (GRAS) product by global regulatory authorities and would not need a pharmaceutical regulatory process as an Rx product in order to reach the market immediately.

In a specific embodiment, the disease or condition treated by co-administration of spilanthol and at least one cannabinoid and/or *cannabis* (e.g., *cannabis* extract or oil) is non-alcoholic fatty liver disease (NAFLD). In some embodiments, NAFLD is simple fatty liver (NAFL) or non-alcoholic steatohepatitis (NASH). In some embodiments, NAFLD comprises NASH. In some embodiments, NAFLD is NASH. In some embodiments, NASH is a form of NAFLD. In some embodiments, the disease, disorder or medical condition that is treatable, curable, mitigated or alleviated by any of the compositions provided herein is NASH. In some embodiments, co-administration of spilanthol and at least one cannabinoid results in a therapeutic effect on NASH. Non-alcoholic fatty liver disease describes a range of conditions caused by a build-up of fat within liver cells. It is very common and in many cases is linked to being obese or overweight. In some people, the build-up of fat in the liver can lead to serious liver disease. This liver disease may be NASH. All people with non-alcoholic fatty liver disease have an increased risk of developing cardiovascular problems such as heart attacks and stroke. Co-administration of spilanthol (e.g., purified form plant material or chemically synthesized), spilanthol-containing extract and/or spilanthol-containing essential oil, and cannabinoids and/or *cannabis* (e.g., *cannabis* extract or *cannabis* oil) can alleviate or decrease accumulation of fat in the liver.

As used herein, the term "NASH" refers to a form of NAFLD that comprises inflammation of the liver and liver damage in addition to fat in the liver. In some embodiments, NASH is fibrotic NASH. In some embodiments, NASH is non-fibrotic NASH. In some embodiments, NASH is cirrhotic NASH. In some embodiments, NASH is non-cirrhotic NASH.

In some embodiments, the disease or condition treated by co-administration of spilanthol and at least one cannabinoid and/or *cannabis* (e.g., *cannabis* extract or *cannabis* oil) is cancer, for example, a brain tumor such as glioma, the most common and most aggressive of the primary brain tumors.

The spilanthol and cannabinoids and/or *cannabis* (e.g. *cannabis* extract or *cannabis* oil) containing compositions described herein may have a direct anti-cancer effect, namely, the combination of spilanthol and *cannabis*/cannabinoids may induce the selective apoptosis and necrosis of cancer cells and thus work as a direct anti-cancer drug.

In addition, the spilanthol and cannabinoids and/or *cannabis* (e.g. *cannabis* extract or *cannabis* oil) containing compositions described herein may have enhancement effects as add-on therapy to existing, or under development, cancer drugs, including chemotherapy drugs, targeted anti-cancer drugs and immune oncology drugs such as programmed death 1 (PD-1) inhibitors and others. In each case, the combined therapy of a composition as described herein together with the specific anti-cancer drug may increase the over-all efficacy of the treatment and, furthermore, increase the response rate of patients to the therapy. For example, an immune-oncology therapy that has a typical low response rate of patients, may be effective in a higher percentage of the patients when administered together with a combined cannabinoids-spilanthol composition.

A dual or combined therapy comprising an immune-oncology (IO) drug (e.g., Keytruda, by Merck), which is considered as the one of the leading anti-cancer therapies in today's oncology clinics, and a composition comprising spilanthol and at least one cannabinoid as described herein, allows achieving higher efficacy with lower dosages of IO drugs, and reduced toxic effects for patients. Such a combined therapy can even totally eradicate the tumors of certain patients.

According to a specific embodiment, the subject treated with the composition is a human being, though veterinary indications are also contemplated herein.

The subject may suffer from the disease or be at risk of having it. The subject may be of any gender or age.

By another aspect, there is provided a method of treating or ameliorating non-alcoholic steatohepatitis (NASH) in a subject in need thereof, comprising co-administering to the subject a therapeutically effective amount of cannabidiol (CBD) and a therapeutically effective amount of spilanthol As used herein, the terms "administering," "administration," and like terms refer to any method which, in sound medical practice, delivers a composition containing an active agent to a subject in such a manner as to provide a therapeutic effect. One aspect of the present subject matter provides for intravenous administration of a therapeutically effective amount of a composition of the present subject matter to a patient in need thereof. Other suitable routes of administration can include dermal, parenteral, subcutaneous, oral, or intrahepatic.

The term "therapeutically effective amount" refers to an amount of a drug effective to treat at least one symptom of a disease or disorder in a mammal. The term "a therapeutically effective amount" refers to an amount effective, at dosages and for periods of time necessary, to achieve the desired therapeutic or prophylactic result. The exact dosage form and regimen would be determined by the physician according to the patient's condition. In some embodiments, a therapeutically effective amount of CBD is administered. In some embodiments, a therapeutically effective amount of spilanthol is administered. In some embodiments, the a therapeutically effective amount of CBD and spilanthol is administered. It will be understood by a skilled artisan that CBD and spilanthol work synergistically, and therefore the therapeutically effective amount is the amount that is effective when the two drugs are co-administered.

In some embodiments, the CBD is in a pharmaceutical composition. In some embodiments, the spilanthol is in a pharmaceutical composition. In some embodiments, the CBD and spilanthol are in a single composition. In some embodiments, the CBD and spilanthol are in separate compositions. In some embodiments, administering a therapeutically effective amount of CBD comprises administering a pharmaceutical composition comprising CBD. In some embodiments, the pharmaceutical composition comprises a therapeutically effective amount of CBD. In some embodiment, administering a therapeutically effective amount of spilanthol comprises administering a pharmaceutical composition comprising spilanthol. In some embodiments, the pharmaceutical composition comprises a therapeutically effective amount of spilanthol.

In some embodiments, the co-administration is administering a single pharmaceutical composition comprising CBD and spilanthol. In some embodiments, the co-administration is administering the CBD and spilanthol separately. In some embodiments, the CBD is administered before the spilanthol. In some embodiments, the CBD is administered after the spilanthol. In some embodiments, the CBD is administered concomitantly with the spilanthol.

In some embodiments, a pharmaceutical composition comprises a pharmaceutically acceptable carrier, excipient or adjuvant. As used herein, the term "carrier," "excipient," or "adjuvant" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N. J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369. In some embodiments, the pharmaceutical composition is a fixed-dose composition comprising CBD and spilanthol.

The carrier may comprise, in total, from about 0.1% to about 99.99999% by weight of the pharmaceutical compositions presented herein.

In some embodiments, the treating and/or ameliorating comprises reducing at least one symptom of the disease. In some embodiments, the at least one symptom of NASH is selected from: increased activity of at least one liver enzyme, increased levels of at least one pro-inflammatory cytokine, and liver weight loss. In some embodiments, the at least one symptom is increased activity of at least one liver enzyme. In some embodiments, the at least one symptom is increased levels of at least one pro-inflammatory cytokine. In some embodiments, the at least one symptom is liver weight loss. In some embodiments, the method further comprises confirming reduction of at least one symptom.

In some embodiments, increased activity of at least one liver enzyme is increased activity of at least one circulating liver enzyme. In some embodiments, a circulating liver enzyme is in the blood. In some embodiments, blood is serum. In some embodiments, increased activity of at least one liver enzyme is increased activity in the liver. In some embodiments, liver enzyme activity is measured in the blood. In some embodiments, liver enzyme activity is measured in the liver. In some embodiments, the method further comprises taking a blood sample. In some embodiments, the method further comprises taking a liver biopsy.

In some embodiments, the at least one liver enzyme is selected from alanine aminotransferase and aspartate aminotransferase. In some embodiments, the at least one liver enzyme is alanine aminotransferase. In some embodiments, the at least one liver enzyme is aspartate aminotransferase.

In some embodiments, the pro-inflammatory cytokine is IL-6. In some embodiments, increased levels are increased expression levels. The term "expression" as used herein refers to the biosynthesis of a gene product, including the transcription and/or translation of said gene product. Thus, nucleic acid expression may refer to transcription of the nucleic acid fragment (e.g., transcription resulting in mRNA or other functional RNA) and/or translation of RNA into a precursor or mature protein (polypeptide). In some embodiments, expression refers to RNA expression. In some embodiments, expression refers to protein expression. In some embodiments, increased levels are in blood. In some embodiments, increased levels are in the liver. In some embodiments, increased levels are in liver-proximal tissue.

In some embodiments, liver weight loss comprises liver damage. In some embodiments, liver damage is cellular damage. In some embodiments, cellular damage comprises cell death. Liver damage and weight loss can be assessed by any method known in the art, including but not limited to ultrasound, MRI, and biopsy.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "10 µm" is intended to mean "about 10 µm".

As used herein, numerical ranges preceded by the term "about" should not be considered to be limited to the recited range. Rather, numerical ranges preceded by the term "about" should be understood to include a range accepted by those skilled in the art for any given element in microcapsules or formulations according to the present invention.

The term "about" as used herein means within an acceptable error range for a particular value as determined by one of ordinary skill in the art, which will depend in part on how the value is measured or determined, i.e., the limitations of the measurement system. For example, "about" can mean a range of up to 10%, more preferably up to 5%, and still more preferably up to 1% of a given value. Where particular values are described in the application and claims, unless otherwise stated, the meaning of the term "about" is within an acceptable error range for the particular value.

The terms "comprises", "comprising", "includes", "including", "having" and their conjugates mean "including but not limited to".

The term "consisting of" means "including and limited to".

The term "consisting essentially of" means that the composition, method or microcapsules may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include chemical, molecular and biochemical, techniques. Such techniques are thoroughly explained in the literature. General references are provided throughout this document. The procedures therein are believed to be well known in the art and are provided for the convenience of the reader. All the information contained therein is incorporated herein by reference.

Materials and Methods (i) Spilanthol-Containing Plant Extracts

Root Extract.

For the preparation of *H. longipes* root extracts, air dried *H. longipes* roots were ground to a fine powder, and the ground plant material (10 g) was subjected to maceration with either dichloromethane or absolute ethanol for one week in a 1:10 ratio (w/v). This process was repeated three times with fresh solvent. Thereafter, the plant material was filtered and the solvents were removed by rotary evaporation under reduced pressure.

Flower Extract.

For the preparation of flowers extract, air-dried flower heads of *Acmella oleracea* are ground and subjected to maceration as described, for example, in U.S. Patent Application Publication Nos. 2008/0050500 U.S. 2011/0104361 and U.S. 2012/156351.

(ii) Purified Spilanthol: Dichloromethane Extraction of Spilanthol Obtained from *H. longipes* Roots Purification of Root Extract.

Dried and ground plant material (7 kg) obtained from *H. longipes* Roots is extracted with dichloromethane as described above. One hundred grams of the dichloromethane extract are fractionated by column chromatography on normal phase using Silica gel as absorbent. In an exemplary embodiment, an open silica gel column is used with hexane and ethyl acetate as eluents in ratios from 100:0 to 40:60 (e.g., 100:0, (80:20, 70:30, 60:40, 40:60, 50:50, 40:60 v/v). Around 400 fractions (250 ml) are collected, monitored by thin layer chromatography (TLC), and grouped into about 20 pools according to their chromatographic similarity. TLC analysis (20×20 cm silica gel on glass plates with a solvent system hexane:ethyl acetate) of pools that revealed the presence of a main dark gray spot (Rf=0.3, hexane:ethyl acetate 3:2 v/v), are visualized with an ultraviolet lamp at 254 nm. Spraying TLC plates with a spray solution of anis aldehyde/sulfuric acid develops a bright purple spot, as reported for other olefinic isobutyl-amides.

In accordance with the above-described exemplary embodiment, pools are combined (45 g) and further analyzed by open column chromatography using a step gradient of hexane and ethyl acetate 100:0 to 90:10. Based on their chromatographic similarity, determined by TLC, fractions eluted with hexane:ethyl acetate 97:3 are combined and evaporated to dryness in vacuo leaving a residue of an apparently pure compound. The purity of the isolated compound is confirmed by HPLC-PDA, using an HPLC chromatograph coupled to a photodiode array detector. The flow rate of the mobile phase (acetonitrile/water 44:56 v/v) is 0.5 ml/min with column temperature of 30° C. and detection wavelength of 229 nm.

Purification of Flower Extracts.

n-hexane extract (200 g) of flower heads prepared as described above, is chromatographed on a silica gel column to separate 36 fractions. Combined relevant fractions are eluted with 10% EtOAc in $CH_2Cl_2$ and re-chromatographed on a silica gel column. The column is eluted with hexane of increasing polarity with acetone to give 60 fractions. The fraction eluted with 10% acetone-hexane is successively chromatographed on a Sephadex LH-20 column with isopropyl alcohol (IPA) and a silica gel column with n-hexane-$CH_2Cl_2$-EtOAc as the eluent to give spilanthol (spilanthol) as oil.

(iii) Determination of the Chemical Structure of Purified Affinin

Chemical structure of the purified spilanthol is elucidated by analysis of its proton nuclear magnetic resonance ($^1$H-NMR) and carbon-13 ($^{13}$C-NMR) spectra (Table 1). Affinin is identified by comparing its spectroscopic constants with those reported in the literature (see, for example, Yasuda et al., *Chem. Pharm. Bull.*, 28: 2251-2253, 1980; Nakatani et al., *Biosci. Biotechnol. Biochem.*, 56: 759-762, 1992).

(iv) *Cannabis* Oil and Purified Cannabinoids

*Cannabis* oil, *cannabis* extracts, and cannabinoids used in accordance with the invention are either purchased or prepared using chemical, molecular and biochemical techniques well taught and known to those skilled in the art. In exemplary embodiment, *cannabis* extracts and cannabinoids are obtained using procedures taught in U.S. Patent Publication No. 2016/0346339, hereby incorporated by reference in its entirety.

Example 1

Acute and Chronic Pancreatitis—In Vitro, In Vivo and Clinical Study Protocols

Acute and chronic pancreatitis are common gastrointestinal disorders that may cause significant morbidity and reduce life expectancy. Despite years of research, the pathogenesis underlying acute pancreatitis (AP) and chronic pancreatitis (CP), and the biological mechanisms of these inflammatory diseases have not been fully elucidated. In addition, there is no known effective medical treatment for this condition. In most cases it is a self-limiting process, yet 20% of patients will develop a severe form of necrosis with multi-organ complications and high risk of mortality.

The endocannabinoid system has been identified recently as a major regulator of physiological and pathological processes, such as pain, inflammation, cell growth, cell death, and as a regulator of diverse gastrointestinal functions. Spilanthol, on the other hand, is known to have activity as a lipase inhibitor, an enzyme that plays a key role in the development of pancreatic inflammatory processes.

Based on this, the present inventor speculated that cannabinoids may play an important role in the pathological process of acute and chronic pancreatitis and as pancreatic anti-inflammatory agents. It has been envisaged by the present inventor that activating these two distinct mechanisms of action, via co-treatment with spilanthol and *cannabis* may result in a synergistic, additive or a mutual potentiating effect in the prevention and treatment of acute and chronic pancreatitis etiologies.

The following goals are set forth: (i) assessing or examining whether a combination therapy of selected cannabinoids and spilanthol may prevent, ameliorate or treat acute and chronic pancreatitis; (ii) span our understanding of the pathophysiological processes governing AP and related complications; and (iii) development of a preventive/therapeutic intervention for human use.

Materials and Methods

In Vitro Model:

selected in vitro acinar cell preparations, such as acinar cell line AR42Jk, as well as pancreatic organoids and slices from mammalian source (ex vivo models), are used to perform a wide-scale, high throughput screening campaign for the potential therapeutic effects in acute pancreatitis of various combinations of cannabinoids and spilanthol. Test assays include $Ca^{2+}$ signaling, intra-acinar protease activation, NF-κB translocation, mitochondrial damage indices, cell injury parameters, and the like. Cannabinoids-spilanthol combinations with the most promising effects are further tested for safety and basic assessment of mode of action.

In Vivo Model:

an established animal model is used to test selected cannabinoid and spilanthol combinations. Preventive and therapeutic potential of such specific combinations are tested in vivo in a mouse model of cerulenin induced pancreatitis (cerulein or cerulenin is a ten amino acid oligopeptide that stimulates gastric, biliary, and pancreatic secretion and is used to induce pancreatitis in experimental animal models).

WT C57 mice are injected intra-peritoneally with cerulein (50 mg/kg, 5 times, at 1-hour intervals) to induce pancreatitis etiology. Mice are divided to 5 study groups as follows: Group 1 (control)—treated with saline only; Group 2—treated with CBD; Group 3—treated with Spilanthol; Group 4—treated with cannabidiol (CBD)+Spilanthol combination; and Group 5—treated with a THC+CBD+Spilanthol combination.

The saline, spilanthol, CBD and test combinations are administered via oral ingestion (gavage), according to the treatment protocol for each group. Pancreatic weight, histological changes (including edema and inflammation), along with blood amylase, lipase and cytokines (IL-6, IL-10, TNF) levels are determined 24 hours following pancreatitis induction for each treatment group. Samples are also collected from lungs and liver. Level of active pancreatitis etiology is determined for each treatment group.

Clinical Assessment:

selected combinations of cannabinoids and spilanthol will be advanced to human clinical studies, with the goal of prevention and treatment of various forms of pancreatitis. The clinical study will enroll 200-300 patients with acute pancreatitis, chronic pancreatitis, or patients at high risk for developing pancreatitis.

Patients will be randomized to 2 groups—Placebo group and treatment group. Treatment group will receive a CBD+Spilanthol formulation for oral ingestion. Treatment period will be 1-4 weeks, depending on medical condition.

Following, and during the treatment period, level of active disease will be assessed for each group.

Example 2

Inflammatory Bowel Disease (Colitis)—Preclinical Study Results

The efficacy of CBD, spilanthol and a combination of CBD and spilanthol in the treatment of inflammatory bowel disease (IBD) was assessed. The preclinical model of choice was Dextran Sodium Sulphate (DSS) induced colitis.

Study Protocol

Colitis was induced in 10 weeks old female C57BL/6 mice (Harlan laboratories, Israel) by feeding them for 8 days with 1.5% (w/vol) DSS in the drinking water (Peer et al. Science, 319: 627-630, 2008; Dearling et al. IBD 2010; Dearling et al. IBD 2016), Kedmi et al. Nature Nanotechnology, 2018.

Mice were divided into 4 study groups (10 mice in each group): 1. Vehicle treatment group; 2. CBD 50 mg/kg treatment group; 3. Spilanthol 10 mg/kg treatment group; and 4. CBD 50 mg/kg+Spilanthol 10 mg/kg combination treatment group (herein "test combination group"). Treatment was given via gavage daily for 8 days. An additional group of 10 healthy mice served as a positive control arm. Body weight was monitored every other day. At the end of day 9 the animals were sacrificed and colon TNFα levels as well as the total length of the length of colon from the cecum to anus were assayed.

Study Readouts

The following readouts were measured in the study as indicators for assessing the amelioration and the therapeutic efficacy of the different treatments: 1. Changes in body weight, 2. Colon's TNFα levels as measured by ELISA kits (R&D Systems, USA), 3. Total length of colon from cecum to anus, as measured by a blinded veterinary doctor.

Study Results

1. Body Weight Loss:

Mice of the vehicle treatment group lost on average 14.6% of baseline body weight as measured on day 9 of the study. The Spilanthol treatment group showed a similar result with an average loss of 14.6% of body weight, while mice of the CBD treatment group lost 8.2% on average. However, the combination treatment group lost only 2.9% of body weight on average as measured on day 9 of the study (FIG. 1). While the Spilanthol treatment alone did not show any efficacy signs in improving body weight loss as compared to vehicle group (0% improvement in outcome) and the CBD treatment alone was able to prevent 44% of the weight loss effect caused by the DSS induced colitis condition itself, the combination therapy demonstrated an 80% prevention of the weight loss (FIG. 2). Statistical significance was calculated using one-way ANOVA with Dunnett's multiple comparison post hoc test to compare the combination treatment group with all other study groups with a result of p<0.001. This result demonstrates a clear synergistic therapeutic effect of the Spilanthol and CBD when administered together as a combination therapy, since the ameliorating therapeutic effect of the combination treatment is stronger than the sum of the effects of the two constituents when administered separately (80%>0%+44%).

2. Colon's Tnfα Levels:

The average colon's TNFα level in the healthy mice group (unconditioned by DSS) was measured as 486 pg/ml. The average colon TNFα level in the vehicle treatment group was measured as 1,116 pg/ml, representing a 630 pg/ml increase of TNFα levels as a result of conditioning by DSS as compared to natural baseline levels—a 130% increase, which represents the increase in colon inflammatory factors concentration as a result of the DSS insult. In the single active agent arms, the average colon TNFα level as measured in the Spilanthol treatment group was 980 pg/ml (representing a 101% increase from baseline) and 928 pg/ml were measured in the CBD group (91% increase). However, the average level of colon TNFα in the combination group was measured as 649 pg/ml—an increase of only 33.5% over baseline levels (FIG. 3). In other words, while the Spilanthol treatment alone was able to reduce the TNFα level by 136 pg/ml comparing to vehicle (21.5% reduction of effect) and the CBD treatment alone was able reduce it by 188 pg/ml (30% reduction), the combination therapy demonstrated an ability to reduce the colon TNFα level by 467 pg/ml comparing to vehicle, which represents a 74% reduction in the TNFα increase effect (FIG. 4). Statistical significance was calculated using one-way ANOVA with Dunnett's multiple comparison post hoc test to compare the combination treatment group with all other study groups with a result of p<0.001. This result further demonstrates a synergistic therapeutic effect of the Spilanthol and CBD when administered together as a combination therapy, since the ameliorating therapeutic effect of the combination treatment is stronger than the sum of the effects of the two constituents when administered separately (74%>21.5%+30%).

3. Total Length of Colon from Cecum to Anus:

The average colon length as measured in the healthy mice group (unconditioned by DSS) was 7.66 cm. The average colon length in the vehicle treatment group was measured as 4.9 cm, representing a 2.76 cm decrease of colon length as a result of conditioning by DSS as compared to natural baseline lengths—a 36% decrease. The average colon length as measured in the Spilanthol treatment group was 4.9 cm (representing a 36% decrease from baseline—the same like vehicle) and an average colon length of 5.31 cm was measured in the CBD group (a 30.7% decrease). However, the average colon length as measured in the combination treatment group was 6.07 cm—representing a decrease of only 20.7% from average baseline length (FIG. 5). In other words, while the Spilanthol treatment alone didn't show any efficacy in reducing the colon shortening effect at all (0% improvement in outcome) and the CBD treatment alone was able to reduce the effect by 0.41 cm (14.9% improvement in outcome), the combination therapy demonstrated an ability to reduce the colon shortening effect by 1.59 cm, which represents a 57.6% improvement in outcome (FIG. 6). Statistical significance was calculated using one-way ANOVA with Dunnett's multiple comparison post hoc test to compare the combination treatment group with all other study groups with a result of p<0.001. This result again further demonstrates a synergistic therapeutic effect of the Spilanthol and CBD when administered together as a combination therapy, since the ameliorating therapeutic effect of the combination treatment is stronger than the sum of the effects of the two constituents when administered separately (57.6%>0%+14.9%).

Conclusion

Three different readouts that measure the potential therapeutic effects of spilanthol alone, CBD alone and the combination thereof were examined for the amelioration of the deleterious effects caused by a DSS induced colitis condition in mice. All three examined parameters showed a clear synergistic effect between the two active agents, with the combined therapy achieving better results than the sum of the improvement results achieved by any of them when administered separately, with a strong statistical significance. This result demonstrates the potential superior and synergistic therapeutic efficacy that can be achieved by using these two active agents spilanthol and CBD as a combined therapy as compared to each of them separately.

Example 3

Irritable Bowel Syndrome (IBS)—Clinical Study Protocol

Irritable bowel syndrome (IBS) is the most common functional gastrointestinal (GI) disorder with worldwide prevalence rates estimated in the range of 10%-15% of the population. IBS is typically a chronic life-long condition with the most common symptoms being abdominal pain or cramping, a bloated feeling and gas, alternating periods of persistent diarrhea or constipation and mucus in the stool.

IBS is one of the most common disorder diagnosed by gastroenterologists and accounts for up to 12% of total visits to primary care providers.

The clinical study set forth the following goals: (i) determining the efficacy of CBD and spilanthol as a combination therapy for the treatment of IBS; and (ii) determining sub-groups of patients that may respond more favorably to the CBD+spilanthol therapy.

Study Population and Enrollment Target.

One hundred (100) to one hundred fifty (150) patients diagnosed with chronic IBS are to be enrolled to the study in a double-blind, placebo-controlled study design. Patients are randomized so that half receive CBD+spilanthol therapy for a period of 8-12 weeks, and the other half receive a placebo treatment for the same period of time.

Patients are to be sub-grouped according to the following criteria:
Disease etiology: diarrhea predominant, constipation predominant, alternating periods of diarrhea and constipation.
psychiatric co-morbidity: anxiety, catastrophism, past trauma, somatization.
endemic endocannabinoid levels in the blood (endocannabinoid deficiency)
Data that are collected from the patients include:
clinical data: demographic data, co-morbidities, IBS symptoms questionnaires, quality of life questionnaires;
psychological data—anxiety questionnaires and the like; and
laboratory tests—blood counts and samples, baseline endocannabinoid levels, stool tests and cultures, microbiome samples and profiles, bile salts levels.
Study primary endpoint—a significant improvement in the IBS symptoms score and/or quality of life score over the study period in the treatment group relative to the placebo group.
Study secondary endpoint—identification of sub-group of patients that responds more favorably to the CBD+Spilanthol therapy relative to other sub-groups of patients. Inclusion criteria: Rome III IBS criteria positive, age 18-80, no antibiotic treatment 14 days before enrollment.
Exclusion criteria: serious previous stomach surgery, a diagnosed existing gut morbidity such as IBD, a diagnosed psychiatric condition, other serious co-morbidity.

Example 4

Alleviating the Symptoms of Irritable Bowel Syndrome (IBS) by Co-Administration of *Cannabis* and Spilanthol-Containing Plant Material A subject inflicted with IBS and suffering strong symptoms including cramping, abdominal pain, bloating, gas and diarrhea, was treated with *cannabis* through vaporization to help control the symptoms. Then, the subject was given spilanthol via chewing the dried root of chilcuague plant. Once spilanthol-containing plant material was consumed, the symptom improved dramatically as compared to using *cannabis* alone.

Example 5

Alleviating Chronic Back Pain by Co-Administration of *Cannabis* and Spilanthol-Containing Plant Material A patient inflicted with chronic back pain achieved a much better control over the pain once he combined chewing of chilcuague dried root with smoking *cannabis* as compared to treatment by smoked *cannabis* alone.

Example 6

Alleviating Chronic Throat Infections by Co-Administration of *Cannabis* and Spilanthol-Containing Plant Material A patient inflicted with chronic throat infections, has combined spilanthol consumption (through chewing of dried chicuague root) with high oral CBD consumption and achieved a much better control over the chronic and repeating infections, as compared to treatment using CBD and spilanthol-containing plant material, each alone.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Example 7

Non-Alcoholic Steatohepatitis (NASH)-Preclinical Study Design and Results

The efficacy of CBD, Spilanthol and a combination of CBD and Spilanthol in the prevention and treatment of non-alcoholic steatohepatitis (NASH) was assessed. The preclinical model of choice was NASH induced by a methionine and choline deficient (MCD) diet.

Study Protocol

MCD diet in mice is considered a common gold standard model for the development of NASH. In this model, the absence of methionine leads to hepatic injury, inflammation, and fibrosis, and the deficiency of choline leads to macrovesicular steatosis. The MCD diet mouse model has been used in several studies to induce NASH with or without fibrosis.

NASH was induced in 12 weeks old Male FVB/NJ mice fed with the MCD diet for 21 days. Mice were divided into 5 study groups (12 mice in each group):
1. Healthy animal group—No induction of NASH by MCD diet.
2. MCD diet group—with no treatment by either CBD or Spilanthol.
3. CBD alone group—MCD diet+daily CBD 50 mg/kg treatment.
4. Spilanthol alone group—MCD diet+daily Spilanthol 10 mg/kg treatment.
5. Combination treatment group—MCD diet+daily CBD 50 mg/kg and Spilanthol 10 mg/kg treatment.

Treatment was given via gavage daily for 21 days. That is, the MCD diet and treatment were initiated simultaneously, so as to examine the treatments' ability both to prevent and treat NASH. Body weight was monitored every other day. At the end of day 21 the animals were sacrificed, and study readouts as described below were measured.

Study Readouts

The following readouts were measured in the study as indicators for the therapeutic efficacy of the different treatments:
1. 1. Liver enzymes activity levels in the serum (ALT and AST).
2. 2. IL-6 pro-inflammatory cytokine serum levels.
3. 3. Liver weight.

Study Readouts

Figure 7A:
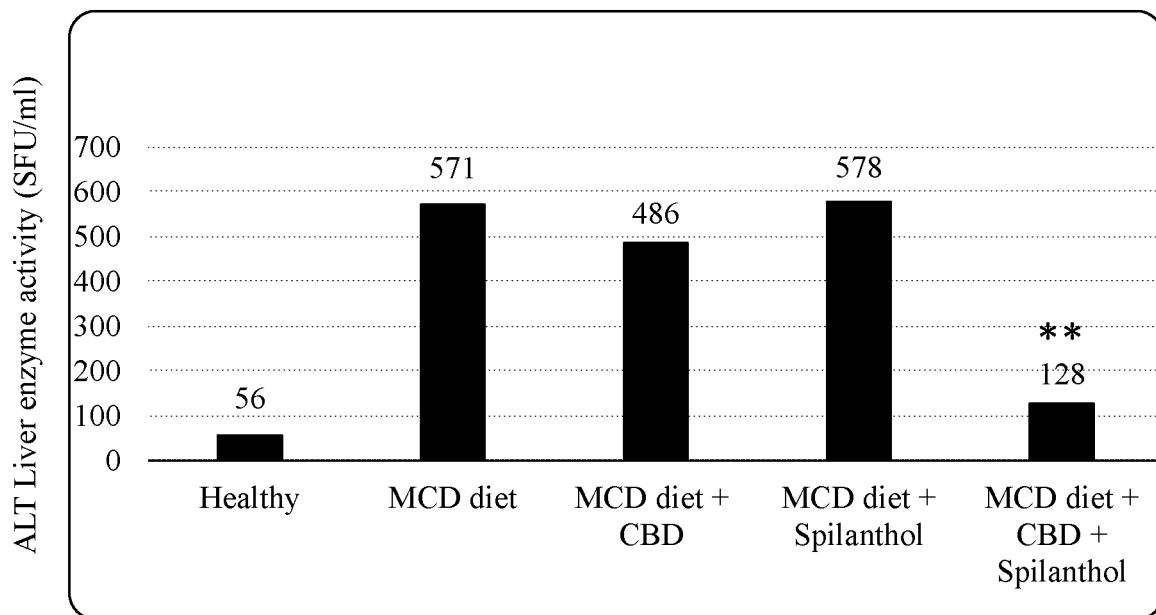
FIG. 7A is a bar chart depicting ALT liver enzyme activity levels in serum from healthy mice and MCD dieted mice with and without treatment. ** indicates significance, with a $p<0.001$.

1. Liver Enzyme Activity Levels in Serum:

The average level of alanine aminotransferase (ALT) activity in the serum of the mice in the different treatment groups was measured using a biochemical autoanalyzer following 21 days of the. The results are summarized in FIG. 7A. The MCD diet without treatment induced a marked elevation of 515 SFU/ml units in the activity index of ALT in the serum of the dieted mice as compared to the not dieted mice. Treatment with CBD alone resulted in a minor non-significant reduction (16.5% reduction of the elevated levels) in ALT serum activity levels. Treatment with Spilanthol alone had no effect on ALT serum activity levels. Nevertheless, the combined treatment of CBD and Spilanthol substantially decreased ALT activity levels (86% reduction of the elevated levels).

Figure 7B:
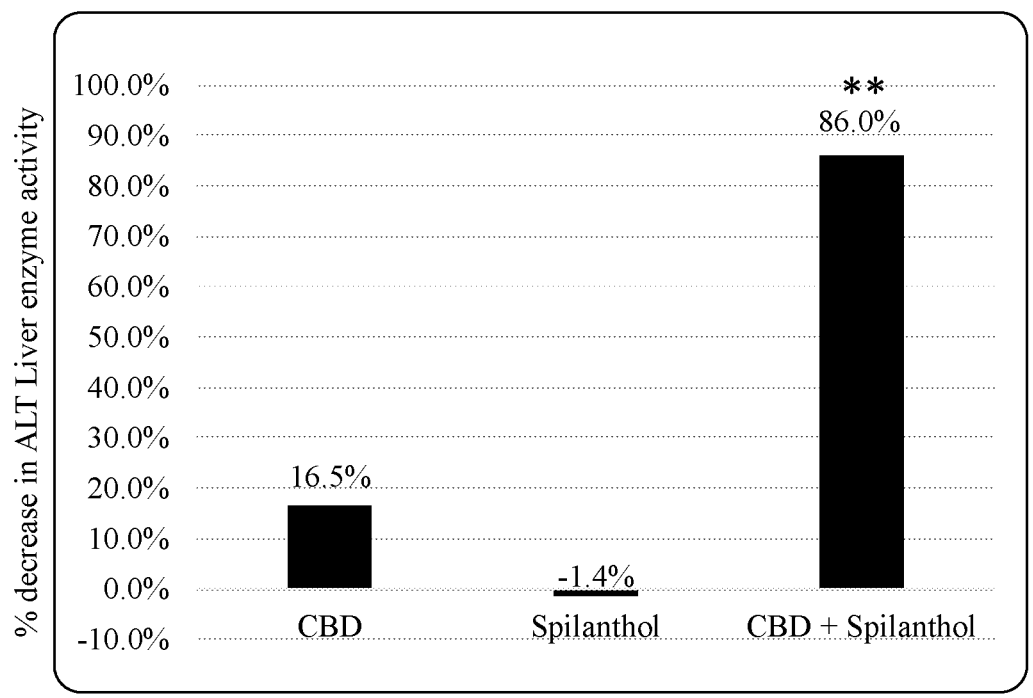
FIG. 7B is a bar chart summarizing the effect seen in FIG. 7A of the three treatments.  indicates significance, with a $p<0.001$

FIG. 7B clearly presents the synergistic effect of combined CBD and Spilanthol treatment, as the combined effect is far more than just additive. Statistical significance was calculated using one-way ANOVA with Dunnett's multiple comparison post hoc test. The reduction caused by combined treatment was highly significant with $p<0.001$, whereas CBD treatment alone was not significant. This result demonstrates a clear synergistic therapeutic effect of Spilanthol and CBD when administered together as a combination therapy, since the ameliorating therapeutic effect of the combination treatment is stronger than the sum of the effects of the two constituents when administered separately.

Figure 8A:
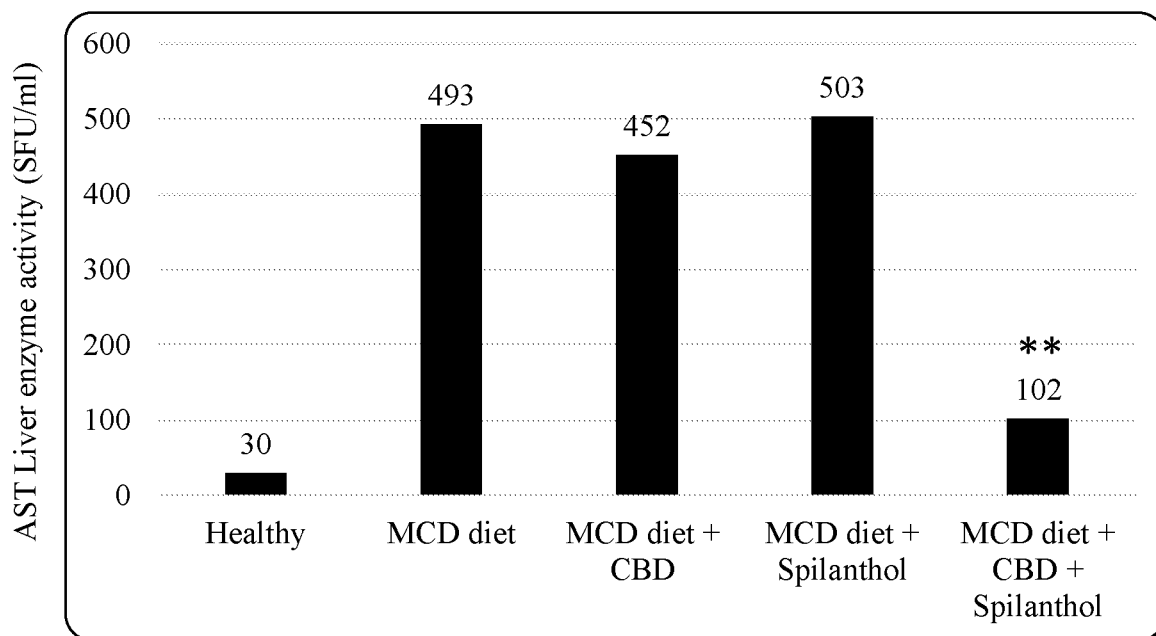
FIG. 8A is a bar chart depicting AST liver enzyme activity levels in serum from healthy mice and MCD dieted mice with and without treatment.  indicates significance, with a $p<0.001$.
Figure 8B:
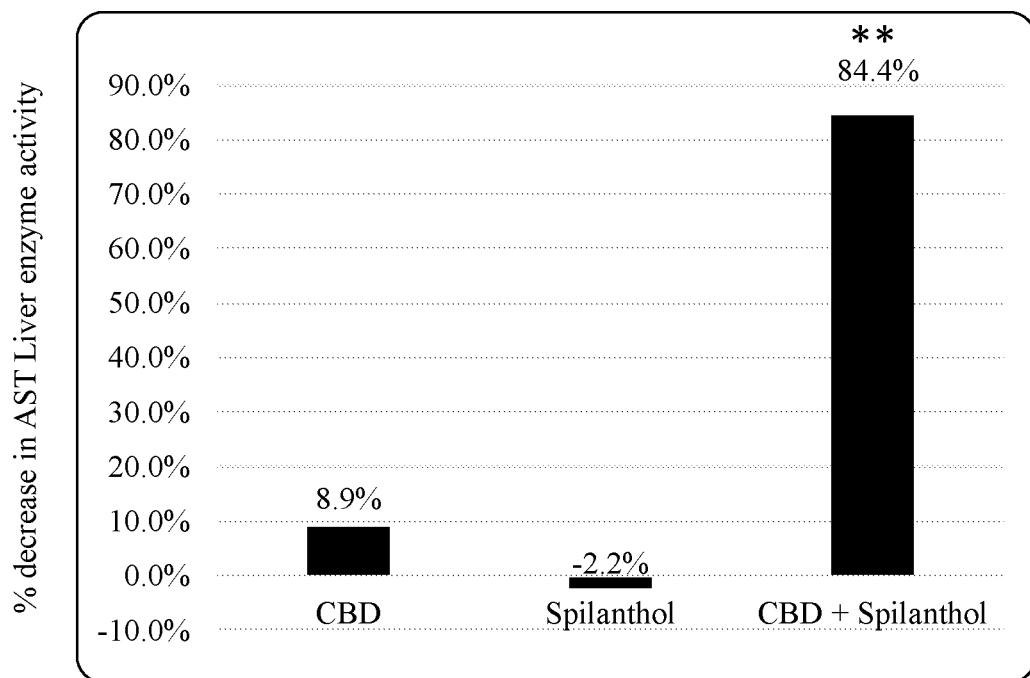
FIG. 8B is a bar chart summarizing the effect seen in FIG. 8A of the three treatments.  indicates significance, with a $p<0.001$

A similar analysis was run for the average activity level of aspartate aminotransferase (AST) in the serum of the tested mice. As shown in FIG. 8A similar results were observed for AST, only in this case neither CBD alone, nor Spilanthol alone has any significant effect, while the combined therapy was highly effective. As can be seen in FIG. 8B, the combined therapy once again produced a greater than 80% reduction in enzyme activity levels. Once again, this reduction was highly statistically significant with $p<0.001$, while the minor reduction seen for CBD alone was not significant. This result demonstrates a clear synergistic therapeutic effect of Spilanthol and CBD when administered together as a combination therapy, since the ameliorating therapeutic effect of the combination treatment is stronger than the sum of the effects of the two constituents when administered separately.

2. IL-6 Pro-Inflammatory Cytokine Serum Levels.

Figure 9A:
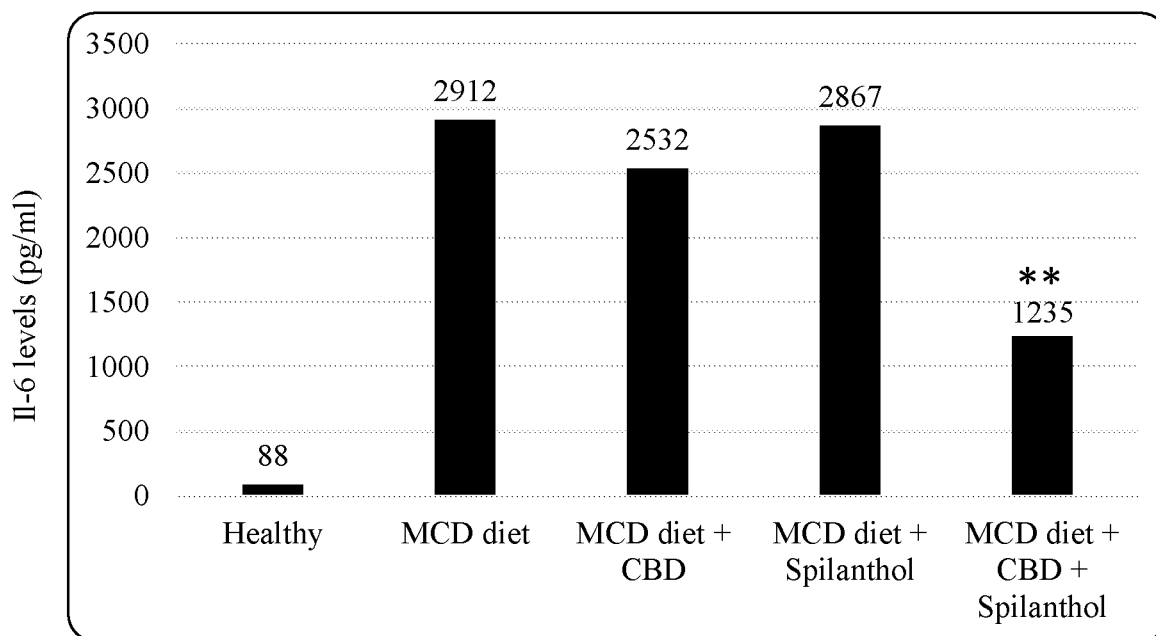
FIG. 9A is a bar chart depicting IL-6 levels in serum from healthy mice and MCD dieted mice with and without treatment.  indicates significance, with a $p<0.001$.

Pro-inflammatory cytokine IL-6 levels were also measured in the serum of the mice at the end of the 21 days of the study using a commercial ELISA kit (R&D systems, USA). FIG. 9A presents the average levels of IL-6 in the different treatment groups. The average level of IL-6 in the serum of the not dieted mice group (healthy) was 88 pg/ml. The average serum IL-6 level in the untreated dieted group was 2,912 pg/ml, representing a 2,824 pg/ml increase as a result of the MCD. CBD treatment caused a minor reduction in IL-6 levels (13.5% reduction of the elevated levels) while Spilanthol was once again ineffective. However, the combination therapy of CBD and Spilanthol resulted in 59.4% in the IL-6 elevated levels.

Figure 9B:
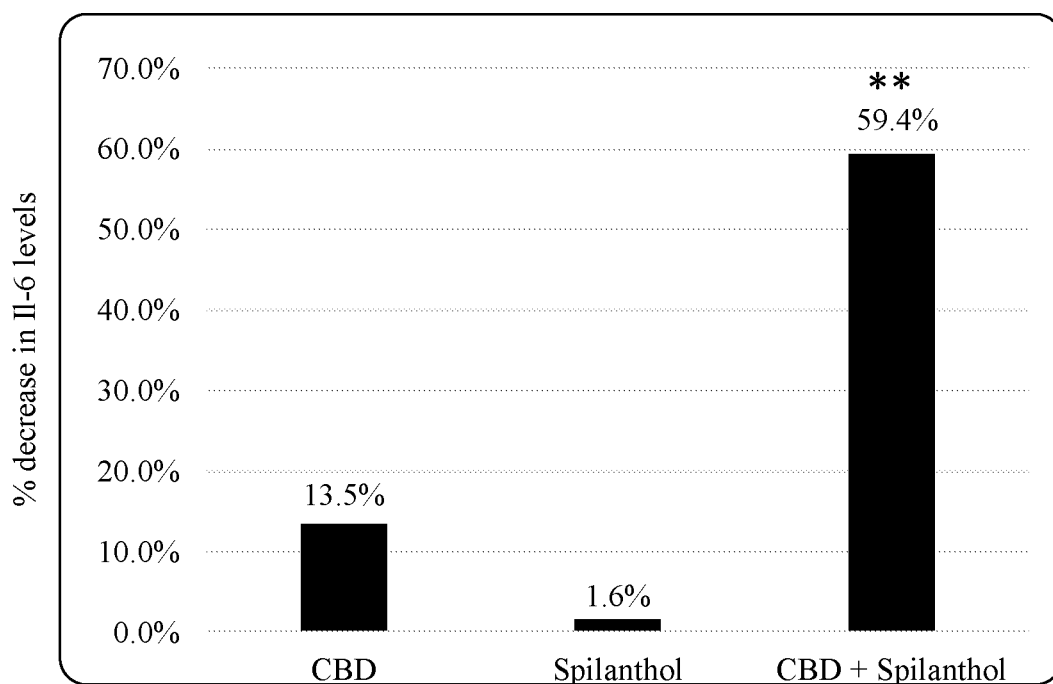
FIG. 9B is a bar chart summarizing the effect seen in FIG. 9A of the three treatments. ** indicates significance, with a $p<0.001$.

FIG. 9B clearly presents the synergistic effect of combined CBD and Spilanthol treatment, as the combined effect of 11-6 levels is far more than just additive. The reduction caused by combined treatment was highly significant with p<0.001, whereas CBD treatment alone was not significant. This result demonstrates a clear synergistic therapeutic effect of Spilanthol and CBD when administered together as a combination therapy, since the ameliorating therapeutic effect of the combination treatment is stronger than the sum of the effects of the two constituents when administered separately.

3. Liver Weight Loss.

Figure 10A:
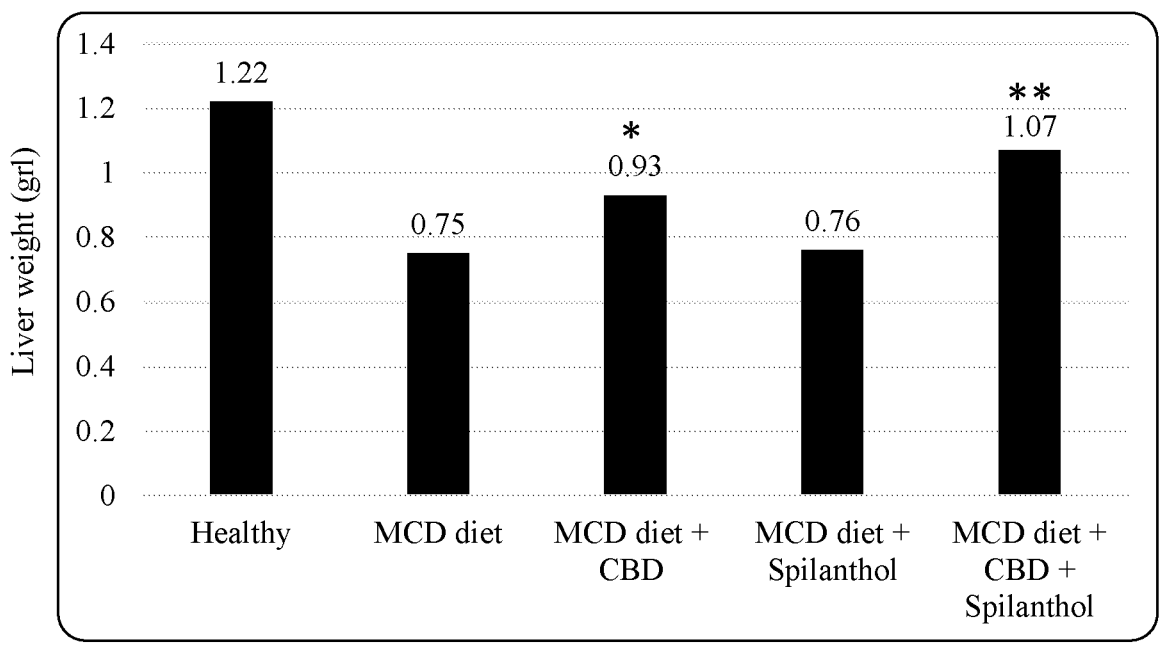
FIG. 10A is a bar chart depicting liver weight from healthy mice and MCD dieted mice with and without treatment. ** indicates significance, with a $p<0.001$, * indicates significance, with a $p<0.01$.

The total liver weight was also measured for all mice following the 21 days of the study. FIG. 10A presents the average liver weight in the different treatment groups. The average liver weight as measured in the not dieted mice group (healthy) was 1.22 grams. The average liver weight in the untreated dieted group was 0.75 grams, with the liver weight loss representing the injury and damage caused to liver tissue as a result of the developing NASH pathology. In the treatment groups, CBD reduced the liver weight loss (38.3% reduction in weight loss), while Spilanthol had no effect. In contrast, the combination treatment caused a surprisingly high 68.1% reduction in liver weight loss, with an average weight of 1.07.

Figure 10B:
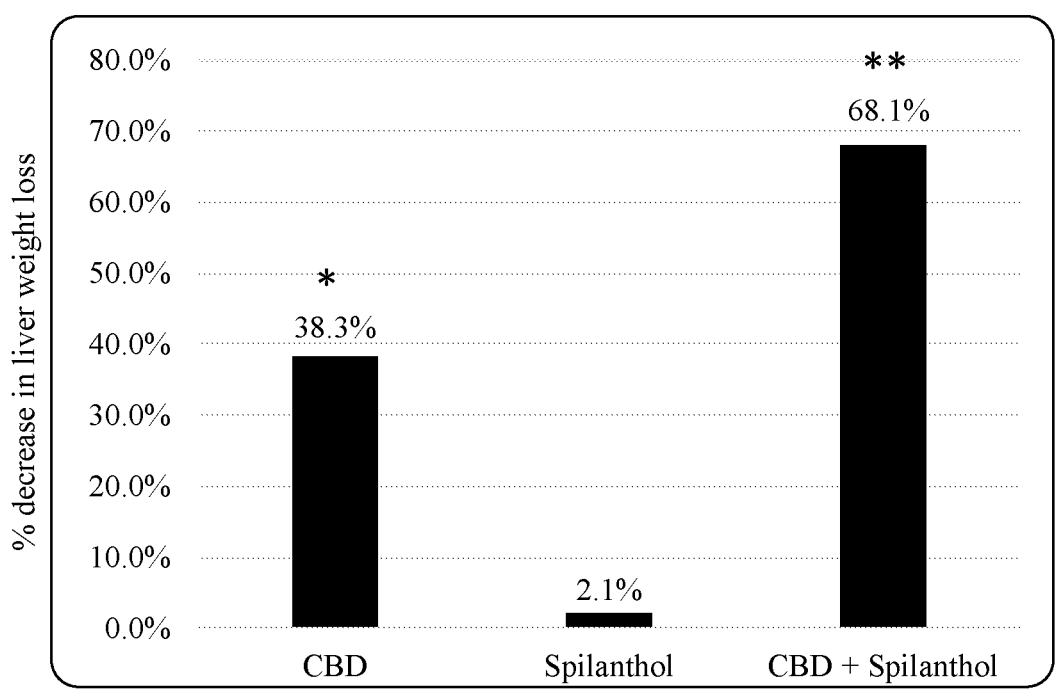
FIG. 10B is a bar chart summarizing the effect seen in FIG. 10A of the three treatments. ** indicates significance, with a $p<0.001$, * indicates significance, with a $p<0.01$.

FIG. 10B clearly presents the synergistic effect of combined CBD and Spilanthol treatment, as the combined effect on liver weight is more than just additive. The reduction in weight loss caused by combined treatment was highly significant with p<0.001, while the reduction caused by CBD alone was significant with a p<0.01. This result demonstrates a clear synergistic therapeutic effect of Spilanthol and CBD when administered together as a combination therapy, since the ameliorating therapeutic effect of the combination treatment is stronger than the sum of the effects of the two constituents when administered separately.

CONCLUSIONS

Four different readouts that measure the potential amelioration of the deleterious effects of NASH-like pathology were examined in the study animals. All four parameters showed a clear synergistic activity between the two active agents, with the combined therapy achieving better results than the sum of the improvement results for each therapy administered separately. Indeed, de novo effects were observed for at least one readout (AST activity levels), and possibly for others, as some of the effects of CBD alone were on the borderline of statistical significance. These results demonstrate the superior and synergistic therapeutic efficacy that can be achieved by using CBD and Spilanthol as a combined therapy in the treatment of NASH.

What is claimed is:

1. A method of treating non-alcoholic steatohepatitis in a human in need thereof, consisting essentially of administering therapeutically effective amounts of at least 95% pure cannabidiol and at least 95% pure spilanthol to said human in need thereof to effectively treat the non-alcoholic steatohepatitis in the human in need thereof.

2. The method of claim 1, wherein said cannabidiol is in a pharmaceutical composition.

3. The method of claim 1, wherein said spilanthol is in a pharmaceutical composition.

4. The method of claim 1, wherein said administering is administering a pharmaceutical composition of both the cannabidiol and the spilanthol.

5. The method of claim 4, wherein said pharmaceutical composition is a fixed-dose composition.

6. The method of claim 1, wherein said cannabidiol and spilanthol are administered separately.

7. The method of claim 1, wherein said spilanthol is an olefinic isobutylamide with the molecular formula of $C_{14}H_{23}NO$.

8. The method of claim 1, wherein said spilanthol is an isomer of formula (1):

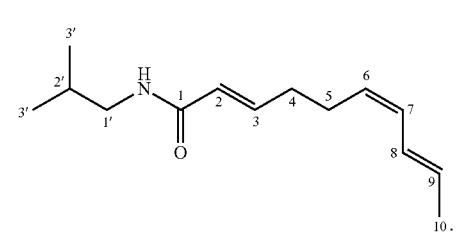

9. The method of claim 1, wherein said therapeutically effective amount of cannabidiol is from 5 mg to 500 mg.

10. The method of claim 1, wherein said therapeutically effective amount of spilanthol is from 1 mg to 100 mg.

11. The method of claim 1, wherein said non-alcoholic steatohepatitis is fibrotic or non-fibrotic.

12. The method of claim 1, wherein said non-alcoholic steatohepatitis is cirrhotic or non-cirrhotic.

13. The method of claim 1, wherein said cannabidiol is administered before, after or concomitantly with said spilanthol.

14. The method of claim 1, wherein said treating reduces at least one symptom of non-alcoholic steatohepatitis, wherein said symptom is selected from the group consisting of:
   a. increased activity of at least one liver enzyme;
   b. increased levels of at least one pro-inflammatory cytokine; and
   c. liver weight loss.

15. The method of claim 14, wherein said at least one liver enzyme is selected from the group consisting of alanine aminotransferase and aspartate aminotransferase.

16. The method of claim 14, wherein said pro-inflammatory cytokine is IL-6.

* * * * *